US005817491A

United States Patent [19]
Yee et al.

[11] Patent Number: 5,817,491
[45] Date of Patent: Oct. 6, 1998

[54] VSV G PSEUSDOTYPED RETROVIRAL VECTORS

[75] Inventors: Jiing-Kuan Yee, Del Mar; Nobuhiko Emi, Nagoya; Theodore Friedmann, La Jolla; Douglas J. Jolly, Leucadia; Jack R. Barber, San Diego, all of Calif.

[73] Assignees: The Regents of the University of California, Oakland; Chiron Viagene, Inc., Emeryville, both of Calif.

[21] Appl. No.: 361,839

[22] Filed: Dec. 22, 1994

Related U.S. Application Data

[63] Continuation-in-part of Ser. No. 344,743, Nov. 23, 1994, abandoned, and Ser. No. 283,704, Aug. 1, 1994, which is a continuation of Ser. No. 114,288, Aug. 30, 1993, abandoned, which is a continuation of Ser. No. 740,766, Aug. 8, 1991, abandoned, which is a continuation-in-part of Ser. No. 658,632, Feb. 19, 1991, abandoned, said Ser. No. 344,743, is a continuation of Ser. No. 139,994, Oct. 20, 1993, abandoned, which is a continuation of Ser. No. 965,084, Oct. 22, 1992, abandoned, which is a continuation of Ser. No. 586,603, Sep. 21, 1990, abandoned.

[51] Int. Cl.$^6$ .............................. C12N 15/86; C12N 5/10; C12N 5/08
[52] U.S. Cl. .................................. 435/172.3; 435/320.1; 435/325; 435/366; 424/93.2
[58] Field of Search .............................. 435/172.3, 320.1, 435/240.1, 240.2, 325, 326; 424/93.2

[56] References Cited

U.S. PATENT DOCUMENTS

| | | | |
|---|---|---|---|
| 4,405,712 | 9/1983 | Vande Woude et al. | 435/69.1 X |
| 4,650,764 | 3/1987 | Temin et al. | 435/350 |
| 4,708,818 | 11/1987 | Montagnier et al. | 435/5 |
| 4,725,669 | 2/1988 | Essex et al. | 530/322 |
| 4,861,719 | 8/1989 | Miller | 435/236 |
| 4,868,116 | 9/1989 | Morgan et al. | 435/373 |
| 4,980,286 | 12/1990 | Morgan et al. | 435/172.3 |
| 4,980,289 | 12/1990 | Temin et al. | 435/235.1 |
| 5,081,029 | 1/1992 | Zarling et al. | 435/172.3 |

FOREIGN PATENT DOCUMENTS

| | | |
|---|---|---|
| 0 178 220 A2 | 4/1986 | European Pat. Off. . |
| 0 243 204 A2 | 10/1987 | European Pat. Off. . |
| 0 245 136 A1 | 11/1987 | European Pat. Off. . |
| 0 273 782 A1 | 7/1988 | European Pat. Off. . |
| 0 293 181 A1 | 11/1988 | European Pat. Off. . |
| WO 86/00922 | 2/1986 | WIPO . |
| WO 89/01516 | 2/1989 | WIPO . |
| WO 89/02468 | 3/1989 | WIPO . |
| WO 83/05349 | 6/1989 | WIPO . |
| WO 89/05345 | 6/1989 | WIPO . |
| WO 89/07150 | 8/1989 | WIPO . |
| WO 90/02806 | 3/1990 | WIPO . |
| WO 90/05538 | 5/1990 | WIPO . |
| WO 90/11092 | 10/1990 | WIPO . |
| WO 90/12087 | 10/1990 | WIPO . |
| WO 90/15141 | 12/1990 | WIPO . |
| WO 91/02805 | 3/1991 | WIPO . |
| WO 91/06658 | 5/1991 | WIPO . |

OTHER PUBLICATIONS

Adam, M.A. and Miller, D.A., "Identification of a Signal in a Murine Retrovirus That is Sufficient for Packaging of Nonretroviral RNA into Virions", *J. Virology* 62(10):3802–3806 (1988).

Aldovini, A. and Young, R.A., Humoral and cell–mediated immune responses to live recombinant BCG–HIV vaccines, *Nature* 351:479–482 (1991).

Altmann, D.M. et al., "Cotransfection of ICAM–1 and HLA–DR reconstitutes human antigen–presenting cell function in mouse L cells", *Nature* 338:512–514 (1989).

Ameisen, J.C. and Capron, A., "Cell dysfunction and delpetion in AIDS: the programmed cell death hypothesis", *Immunol. Today* 12:102–105 (1991).

Anderson, K.D. et al., "Gene expression in implanted rat hepatocytes following retroviral–mediated gene transfer", *Somat Cell Mol. Genet.* 15:215–227 (1989).

Anderson, W.F. "Prospects for human gene therapy", *Science* 226:401–409 (1984).

Armentano, D. et al., "Effect of internal viral sequences on the utility of retroviral vectors", *J. Virol.* 61:1647–1650 (1987).

Arnold et al., *J. Cell Biochem. L401*:145 (1990).

Baltimore, D., "Gene therapy. Intracellular immunization", *Nature* 335:395–396 (1988).

Ban et al., "Bovine Leukaemia Virus Packaging Cell Line for Retrovirus–Mediated Gene Transfer", *J. Gen. Virol.* 70:1987–1993 (1989).

Barnd, D.L. et al., "Specific, major histocompatibility complex–unrestricted recognition of tumor–associated mucins by human cytotoxic T cells", *Proc. Natl. Acad. Sci. USA* 86:7159–7163 (1989).

Baskin, Y., *The Gene Doctors, Medical Genetics at the Frontier Genetics at the Frontier* William Morrow & Co. N.Y. p. 211 (1984).

Bastin et al., *Journal of Experimental Medicine* 165:1508–1523 (1987).

Bender, et al. *J. Virology* 61:1639–1646 (1987).

Berkner, "Development of adenovirus vectors for the expression of heterologous genes", *Biotechniques* 6:616–629 (1988).

Bernards, R. et al., "N–myc amplification causes down-modulation of MHC class I antigen expression in neuroblastoma", *Cell* 47:667–674 (1986).

Bernards, R. et al., "Effective tumor immunotherapy directed against an oncogene–encode product using a vaccinia virus vector", *Proc. Natl. Acad. Sci. USA* 84:6845–6858 (1987).

(List continued on next page.)

Primary Examiner—George C. Elliot
Assistant Examiner—Johnny F. Railey, II
Attorney, Agent, or Firm—Karl Bozicevic; Carol Francis; Bozicevic & Reed

[57] ABSTRACT

An enveloped vector particle contains gag and pol proteins from a retrovirus, a nucleic acid sequence and an envelope that includes VSV G envelope glycoprotein. The vector particle can be used to introduce nucleic acids into cells.

22 Claims, 10 Drawing Sheets

OTHER PUBLICATIONS

Besmer et al., "Mechanism of Restriction of Ecotropic and Xenotropic Murine Leukemia Viruses and Formation of Pseudotypes Between the Two Viruses", *J. Virology* 21(3):965–973 (1977).
Bix et al., *Nature* 349:329–331 (1991).
Bjorkman, P.J. et al., "The foreign antigen binding site and T cell recognition regions of class I histocompatibility antigens", *Nature* 329:512–518 (1987).
Bolognesi, D.P. and Fischinger, P.J., "Prospects for treatment of human retrovirus–associated diseases", *Cancer Res.* 45:4700s–4705s, (1985).
Braakman et al., *Int. J. Cancer* 46:475–480, (1990).
Braciale, T.J. et al., "Antigen presentation pathways to class I and class II MHC–restricted T lymphocytes", *Immunol. Rev.* 98:95–114 (1987).
Braciale, T.J. and Yap, K.L., "Role of viral infectivity in the induction of influenza virus–specific cytotoxic T cells", *J. Exp. Med.* 147:1236–1252 (1978).
Bubenik, J. et al., "Local administration of cells containing an inserted IL–2 gene and producing IL–2 inhibits growth of human tumors in nu/nu mice", *Immunol. Lett.* 19:279–282 (1988).
Carey, *Business Week* pp. 133, 136 (May 1, 1989).
Carr, F. et al., "Genetic transformation of murine bone marrow cells to methotrexate resistance", *Blood* 62:180–185 (1983).
Cepko, C.L. et al., "Construction and applications of a highly transmissible murine retrovirus shuttle vector", *Cell* 37:1053–1062 (1984).
Cepko C., "Retrovirus vectors and their applications in neurobiology", *Neuron* 1:345–353 (1988).
Chakrabarti, S. et al., "Expression of the HTLV–III envelope gene by a recombinant vaccinia virus", *Nature* 320:535–537 (1986).
Cline et al., "Gene transfer in intact animals", *Nature* 284:422–425 (1980).
Collins, M.K. et al., "Transfer of functional EGF receptors to an IL3–dependent cell line", *J. Cell. Physiol.* 137:293–298 (1988).
Cone, et al., "HLA–DR gene expression in a proliferating human thyroid cell clone (12S)", *Endocrinology* 123:2067–2074 (1988).
Cone, R.D. and Mulligan, R.C., "High–efficiency gene transfer into mammalian cells: generation of helper–free recombinant retrovirus with broad mammmalian host range", *Proc. Nat. Acad. Sci. USA* 81:6349–6353 (1984).
Cortes et al., *J. Surg. Onco.* 25:289–295 (1984).
Crowley, N.J. et al., "Generation of human autologous melanoma–specific cytotoxic T–cells using HLA–A2–matched allogenic melanomas", *Cancer Res.* 50:492–498 (1990).
Culliton, B.J. "Designing cells to deliver drugs", *Science* 246:746–751 (1989).
Dallo, S. et al., "Humoral immune response elicited by highly attenuated variants of vaccine virus and by an attenuated recombinant expressing HIV–1 envelope protein", *Virology* 173:323–329 (1989).
Danos et al., "Safe and Efficient Generation of Recombinant Retroviruses with Amphotropic and Ecotropic Host Ranges", *Proc. Natl. Acad. Sci., USA* 85:6460–6464 (1988).
De Baetselier, P. et al., "Differential expression of H–2 gene products in tumor cells in associated with their metastatogenic properties", *Nature* 288:179–181 (1980).
Delouis et al., "Xenotropic and Amphotropic Pseudotyped Recombinant Retrovirus to Transfer Genes into Cells from Various Species", *Biochem. Biophys. Res. Comm.* 169(1):8–14 (1990).
de Vries, J.E. et al., "Interplay between the TCR/CD3 complex and CD4 or CD8 in the activation of cytotoxic T lymphocytes", *Immunol. Rev.* 109:119–141 (1989).
Dewar, R.L. et al., "Synthesis and processing of human immunodeficiency virus type 1 envelope proteins encoded by a recombinant human adenovirus", *J. Virol.* 63:129–136 (1989).
Earl et al., *J. Virol.* 65:31–41 (1991).
Ellrodt et al., *Nature* 325:765, (1987).
Embertson, J.E. and Temin, H.M., "Pseudotyped Retroviral Vectors Reveal Restrictions to Reticuloendotheliosis Virus Replication in Rat Cells", *J. Virol.* 60:662–668 (1986).
Embertson et al. *J. Virology* 61:2675–2683 (1987).
Emi et al., *J. Cell Biochem. Supl.* 14A:367, Abstract D408.
Emi, N. et al. "Pseudotype Formation of Murine Leukemia Virus with the G Protein of Vesicular Stomatitis Virus", *Journal of Virology,* 65(3):1202–1207 (1991).
Epsikopou et al., *PNAS* 81:4657–4661 (1984).
Estin et al., *PNAS* 85:1052–1056 (1988).
Evans et al., *Nature* 339:385–388 (1989).
Faraji–Shaden et al., *Medical Hypothesis* 32:81–84 (1990).
Fauci et al., *Ann Intern. Med.* 110:373–385 (1989).
Flexner et al., *Virology* 166:339–349 (1988).
Friedmann, *Ann. N.Y. Acad. Sci.* 265:141–152 (1975).
Friedmann, *Science* 244:1275–1281 (1989).
Gansbacher et al., *Cancer Research* 50:7820–7825 (1990).
Gattoni–Celli et al., *PNAS* 85:8543–8547 (1988).
Gilboa et al., *BioTechniques* 4:504–512 (1986).
Gilboa et al., *The Biology of Hematopiesis* pp. 301–311 (1990).
Graham et al., *Virology* 52:456–457 (1973).
Gruber et al., *Science* 230:1057–1061 (1985).
Guarini et al., *Cancer Immunol. Immunother.* 30:262–268 (1989).
Hatzoglou et al., *J. Biol. Chem.* 263:17798–17808 (1988).
Haynes et al., *Science* 260:1279–1286 (1993).
Hellerman et al., *PNAS* 81:5340–5344 (1984).
Hester et al., *J. Nat. Cancer Inst.* 82:1209–1214 (1990).
Hickling et al., *Journal of Virology* 61:3463–3469 (1987).
Hoffenbach et al., *Journal of Immunology* 142:452–462 (1989).
Hopkins, N., "High titers of Retrovirus (vesicular stomatitis virus) pseudotypes, at last", *Proc. Natl. Acad. Sci. USA* 90:8759–8760 (1993).
Hoshino, H. et al., "Human T–cell Leukemia Virus Type I: Pseudotype Neutralization of Japanese and American Isloates with Human and Rabbit Sera", *Int. J. Cancer* 36:671–674 (1985).
Hu et al., *Nature* 328:721–723 (1987).
Hu et al., *Virology* 179:321–329 (1990).
Huang, A.S. et al. "Growth of Pseudotypes of Vesicular Stomatitis Virus with N–Tropic Murine Leukemia Virus Coats in Cells Resistant to N–Tropic Viruses", *J. Virology* 12:659–662 (1973).
Hunt et al., *J. Virology* 62:3014–3019 (1988).
Isobe et al., *J. Nat. Cancer Inst.* 81:1823–1828 (1989).
Jaroff, *Time* pp. 74–76 (Sep. 24, 1990).
Johnston et al., *Science* 260:1286–1293 (1993).
Johnston et al., *Nature* 328:361–353 (1987).
Jolly et al., *Biotechnology Therapeutics* 2(1–2):179–193 (1990–1991).

Jolly et al., *Methods in Enzymology* 149:10–5 (1987).
Jolly et al., *Mol. Cell Biol.* 6:1141–1145 (1986).
Joyner et ak., *Developmental Biology Using Purified Genes, Academic Press* (1981).
Joyner et al., *Nature* 305:556–558 (1983).
Kanoff et al., *J. Exp. Med.* 166:219–234 (1987).
Kasid et al., *PNAS* 87:473–477 (1990).
Kast et al., *Cell* 59:603–614 (1989).
Keller et al., *Nature* 318:149–154 (1989).
Klavinskis et al., *J. Virol.* 63:4311–4316 (1989) .
Koenig et al., *J. Immunol.* 145:127–135 (1990).
Kohn, *Blood Cells* 13:285–298 (1987).
Korman et al., *PNAS* 84:2150–2154 (1987).
Kourilsky et al., *Adv. in Immunol.* 45:107–193 (1989).
Lathe et al., *Nature* 326:878–880 (1987).
Ledley et al., *PNAS* 83:409–413 (1986).
Ledley, *J. Pediatrics* 110:1–8 (1987).
Lee, *Can. Med. Assoc. J.* 134:311–313 (1986).
Li et al. *Virology* 171:331–341 (1989).
Linial, et al., *Cell* 15:1371–1381 (1978).
Linial, *J. Virology* 38:380–382 (1981).
Littlefield et al. *Nature* 11:250–252 (1966).
Livingston, D.M. et al. , "Identification of Infectious Virions which are Vesicular Stomatitis Virus Pseudotypes of Murine Type C Virus", *Virology* 70:432–439 (1976).
Lotteau et al., *J. Exp. Med.* 169:351–356 (1989).
Lotze et al., *Immunology* 11:190–193 (1990).
Love, D.N. et al., "Pseudotypes of Vesicular Stomatitis Virus Determined by Exogenous and Endogenous Avian RNA Tumor Viruses", *Virology* 57:217–278 (1974).
Luytjes et al., *Cell* 59:1107–1113 (1989).
Mandeville R., et al. "Neutralization of pseudotypes of Vesicular Stomatitis Virus by sera from Avian Retrovirus–infected hosts'", *International Journal of Cancer*, 23(3):415–423 (1975).
Mann, R. et al., "Construction of a Retrovirus Packaging Mutant and its Use to Produce Helper–Free Defective Retrovirus", *Cell*33:153–159 (1983).
Mariman, *Nature* 318:414 (1985).
Markowitz, D. et al., "A Safe Packaging Line for Gene Transfer: Separating Viral Genes on Two Different Plasmids", *J. Virology* 62(4):1120–1124 (1984).
Markowitz, D. et al., "Construction and Use of a safe and Efficient Amphotropic Packaging Cell Line", *Virology* 167:400–406 (1988).
Mason et al., *Science* 234:1372–1378 (1986).
McCune et al., *Cancer Immunol. Immunother.* 32:62–66 (1990).
McLachlin, J.R. et al., *Prog. Nucl. Acid. Res. and Mol. Biol.* 38:91–134 (1990).
McMichael et al., *The New England J. Med.* 309:13–17 (1983).
Mercola et al., *Science* 208:1033–1035 (1980).
Merz, *JAMA* 257:150–151 (1987).
Michel et al., *Eur. J. Immunol.* 18:1917–1924 (1988).
Miller, D.A. et al., "Generation of Helper–Free Amphotropic Retroviruses that Transduce and Dominant–Acting, Methotrexate–Resistant Dihydrofolate Reductase Gene", *Mol. Cell. Biol.* 5:431–437 (1985).
Miller et al., *PNAS* 80:4709–4713 (1983).
Miller et al., *Science* 225:630–632 (1984).
Miller, D.A., "Retrovirus Packaging Cells", *Human Gene Therapy* 1:5–15 (1990).

Miller, D.A. et al. "Redesign of Retrovirus Packaging Cell Lines to Avoid Recombinant Leading to Helper Virus Production", *Mol. Cell Biol.* 6(8):2895–2902 (1986).
Mitsuya et al., *Nature* 325:773–778 (1987).
Mohr, M.D. et al., "Detection of VSV (MuLV) Pseudotypes by an Immunobiochemical Technique", *Virology* 117:522–529 (1982).
Moolten et al., *Medical Hypothesis* 24:43–51 (1987).
Morgan et al., *Science* 237:1476–1479 (1987).
Morgenstern, J.P. and Land, H., "Advanced Mammalian Gene Transfer", *Nucl. Acids Res.* 18:3587–3596 (1990).
Morrow, *Ann. N.Y. Acad. Sci.* 265:13–21 (1975).
Mulligan, *Experimental Manipulation of Gene Expression* 8:155–173 (1983).
Nabel et al., *Science* 244:1342–1344 (1989).
Nixon et al., *Nature* 336:484–487 (1988).
Okayama et al. *Mol. Cell Biol.* 3:280–289 (1983).
Orme, I., *M. Journal of Immunology* 138:293–298 (1987).
Overell et al., *Mol. And Cell. Biol.* 8:1803–1808 (1988).
Palmer et al., *PNAS* 88:1330–1334 (1991).
Panicali et al., *PNAS* 80:5364–5368 (1983).
Parnes et al., *PNAS* 78:2253–2557 (1981).
Plata et al., *Nature* 328:348–351 (1987).
Quade et al. *Virology* 98:461–465 (1979).
Reddehase et al., *Journal of Virology* 61:3102–3108 (1987).
Redfield et al., *The New England J. Med.* 324:1677–1684 (1991).
Reif, *Cancer Research* 45:25–31 (1985).
Reimann et al., *J. Immunol. Methods* 89:93–101 (1986).
Roman, L.M. et al., *Experimental Cell Research* 175:376–387.
Rose, J.K. and Bergmann, J.E., "Expression from Cloned cDNA of Cell–Surface and Secreted Form of the Glycoprotein of Vesicular Stomatitis Virus in Eucaryotic Cells", *Cell* 30:753–762 (1982).
Rose et al. *J. Virol.* 39:519–528 (1981).
Rosenberg et al., *The New England J. Med.* 323:570–578 (1990).
Rosenfeld et al., *Science* 252:431–434 (1991).
Rouse et al., *Rev. Infect. Dis.* 10:16–33 (1988).
Rubenstein et al., *PNAS* 81:7137–7140 (1984).
Ruprecht et al., *PNAS* 87:5558–5562 (1990).
Sabin et al., *J. Bio. Standardization* 1:115–118 (1973).
Saito et al., *Immunological Reviews* 101:81–193.
Salk et al., *Nature* 327:473–476 (1987).
Schlegel, R. et al., "Inhibition of VSV Binding and Infectivity by Phosphatidylserine", *Cell* 32:639–646 (1983).
Schnitzer, T.J. et al. "Pseudotypes of Vesicular Stomatitis Virus with the Envelope Properties of Mammalian and Primate Retroviruses", *J. Virology* 23(3):449–454 (1977).
Shimotohno et al., *Cell* 26:67–77 (1981).
Shinitzky and Skornick, *EORTC Genitourinary Group Monograph Basic and Treatment of Renal Cell Carcinoma Metastasis* 9:95–125 (1990).
Simmons et al., *Nature* 331:624–626 (1988).
Siu et al., *J. Immunology* 143:3813–3820 (1989).
Sleckman et al., *Nature* 328:351–353 (1987).
Smith et al., *PNAS* 86:5557–5561 (1989).
Sorge, J. et al., "Amphotropic Retrovirus Vector System for Human Cell Gene Transfer", *Mol. Cell Biol.* 4(9):1730–1737 (1984).
St. Louis et al., *PNAS* 85:3150–3154 (1988).
Stover et al., *Nature* 351:456–460 (1991).
Strair et al., *J. Virology* 62:4756–4759 (1988).
Stuhlmann et al., *PNAS* 81:7151–7155 (1984).

Takahashi et al., *PNAS* 85:3105–3109 (1988).
Takahashi et al., *Science* 246:118–121 (1989).
Tato, F. et al., "A Mutant of Rous Sarcoma Virus with a Thermolabile Defect in the Virus Envelope", *Virology* 88:71–81 (1978).
Tellier et al., *Nature* 318:414 (1985).
Termin, *Science* 246:983 (1989).
Tevethia et al., *Journal of Virology* 107:13–23 (1980).
Thomason and Booth, *Amer. J. Physiology* 258:c578–c581 (1990).
Townsend et al., *Cell* 42:457–467 (1985).
Townsend et al., *Cell* 44:959–968 (1986).
Traversari et al., *J. Immunol.* 142:2887–2894 (1989).
Van Den Eynde et al., *Int. J. Cancer* 44:634–640 (1989).
Vaux et al. *Nature* 336:36–42 (1988).
Verma, *Scientific American* 262:68–72, 81–84 (1990).
Walker et al., *Nature* 328:345–348 (1987).
Walker et al., *Science* 240:64–66 (1988).
Wallich et al., *Nature* 315:301–305 (1985).
Warner et al., *AIDS Research & Human Retroviruses* 7(8):645–655 (1991).
Wantanabe et al., *Mol. Cell. Biol.* 3:2241–2249 (1983).
Wantanabe, J. et al., "Encapsidation Sequences for Spleen Necrosis, an Avian Retrovirus, are Between the 5' Long Terminal Repeat and the start of the gag Gene", *Proc. Nat. Acad. Sci. USA* 79:5986–5990 (1982).
Weber and Jay, *Curr. Top. Microbiol. Immunol.* 137:140–147 (1988).
Weber et al., *J. Exp. Med.* 166:1716–1733 (1987).
Wei et al., *J. Virology* 39:935–944 (1981).
Weis, J.H. et al., *Mol. & Cell. Biol.* 5:1379–1384 (1985).
Weis et al., *PNAS* 81:4879–4883 (1984).
Weiss, R.A. and Bennett, L.P. et al., "Assembly of Membrane Glycoproteins Studied by Phenotypic Mixing between Mutants of Vesicular Stomatitis Virus and Retroviruses", *Virology* 100:252–274 (1980).
Whitt, M.A. et al., "Glycoprotein Cytoplasmic Domain Sequences Required for rescue of a Vesicular Stomatitis Virus Glycoprotein Mutant", *J. Virology* 63:3569–3578 (1989).
Willey, R.L., "In Vitro Mutagenesis Identifies a Region within the Envelope Gene of the Human Immunodeficiency Virus that is Critical for Infectivity", *J. Virology* 62:139–147 (1988).
Wills, J.W. et al., "Mutations of the Rous Sarcoma Virus env Gene that Affect the Transport and Subcellular Location of the Glycoprotein Products", *J. Cell Biol.* 99:2011–2023 (1984).
Wilson, C. et al., "Formation of infectious hybrid virions with gibbon ape leukemia virus and human T–cell leukemia virus retroviral envelope glycoproteins and the gag and pol proteins of Moloney murine leukemia virus", *J. Virology* 63:2374–2378 (1989).
Wilson et all., *Science* 248:1413–1416 (1990).
Wilson, et al. *Science* 244:1344–1346 (1990).
Witte, O.N. and Baltimore, D., "Mechanism of Formation of Pseudotypes Between Vesicular Stomatitis Virus and Murine Leukemia Virus", *Cell* 11:505–511 (1977).
Wolff et al., *PNAS* 86:9011–9014 (1989).
Wong et al., *Genes Dev.* 1:358–365 (1987).
Xu et al., *Virology* 171:331–341 (1989).
Yap et al., *Nature* 273:238–239 (1978).
Zagury et al., *Nature* 326:249–250 (1987).
Zagury et al., *Nature* 332:728–721 (1988).
Zarling et al., *J. Immunol.* 139:988–990 (1987).
Zarling et al., *Nature* 323:344–346 (1986).
Zavada, J., "Pseudotypes of Vesicular Stomatitis Virus with the Coat of Murine Leukemia and of Avian Myeloblastosis Virus", *J. Gen. Virol.* 125:183—191 (1972).
Zavada, J. et al., "Vesicular Stomatitis Virus phenotypically mixed with Retroviruses: an efficient detection method", *Acta Virol.* 27(2):110–118 (1983).
Zbar et al., *Cancer Research* 43:46–53 (1983).
Zinkernagel et al., *Adv. in Immunol.* 27:51–177 (1979).
Zinkernagel et al., *J. Exp. Med.* 145:644–651 (1977).
Zwiebel et al., *Ann. N.Y. Acad. Sci.* 618:394–404 (1980).
Weiss, R.A., et al., "Pseudotypes of Avian Sarcoma Viruses with the Envelope Properties of Vesicular Stomatitis Virus," *Virology* 76:808–825 (1977).

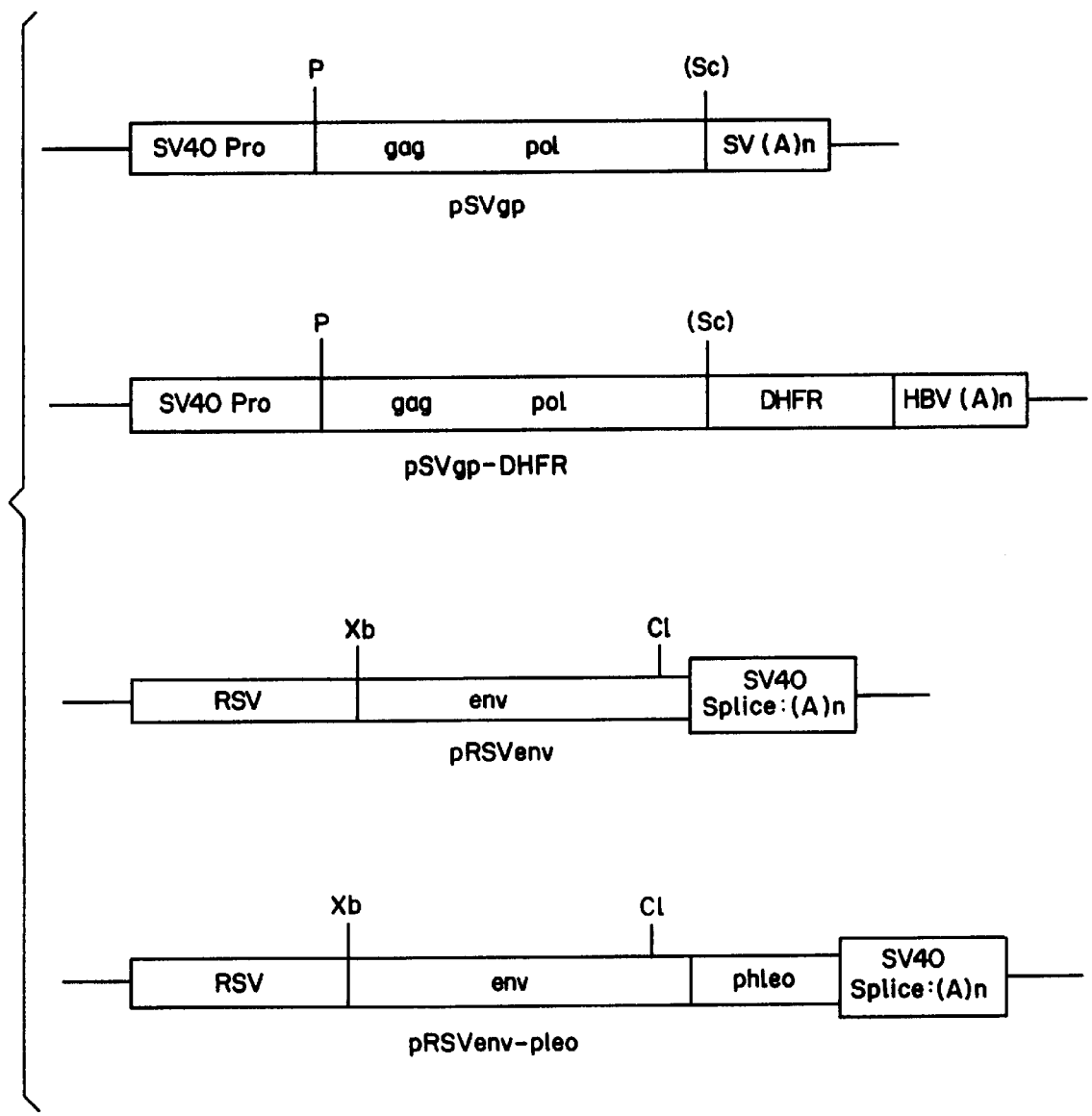
FIG. IA

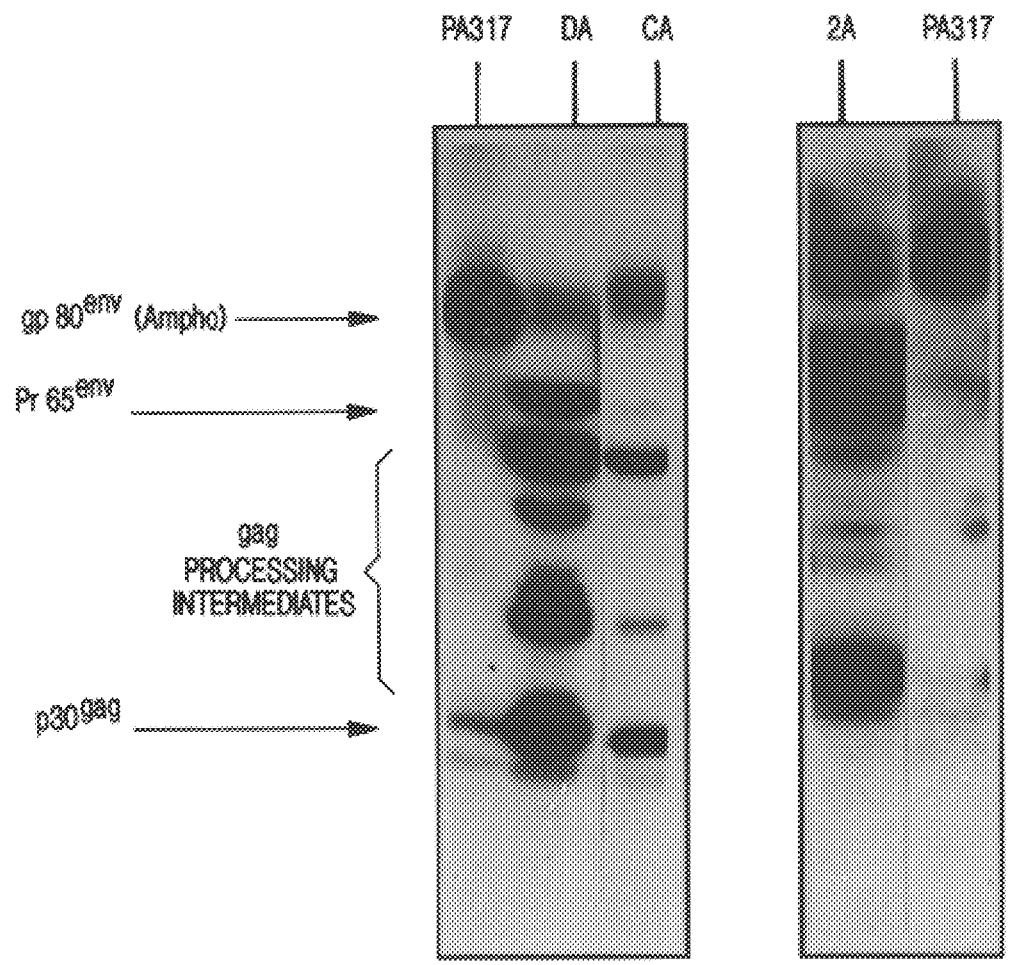
FIG. IE

VSV G PSEUSDOTYPED RETROVIRAL VECTORS

CROSS-REFERENCE TO RELATED APPLICATIONS

This application is a continuation-in-part application of application Ser. No. 08/344,743, filed in the United States Patent and Trademark Office on Nov. 23, 1994, now abandoned, which application is a continuation of U.S. patent application Ser. No. 08/139,994, filed in the United States Patent and Trademark Office on Oct. 20, 1993, now abandoned, which application was a continuation of U.S. patent application Ser. No. 07/965,084, filed in the United States Patent and Trademark Office on Oct. 22, 1992, now abandoned, which application was a continuation of U.S. patent application Ser. No. 07/586,603, filed in the United States Patent and Trademark Office on Sep. 21, 1990, now abandoned; and U.S. patent application Ser. No. 08/283,704, filed in the United States Patent and Trademark Office on Aug. 1, 1994, which application is a continuation of U.S. patent application Ser. No. 08/114,288, filed in the United States Patent and Trademark Office on Aug. 30, 1993, now abandoned, which application was a continuation of U.S. patent application Ser. No. 07/740,766, filed in the United States Patent and Trademark Office on Aug. 8, 1991, now abandoned, which application was a continuation-in-part of U.S. patent application Ser. No. 07/658,632, filed in the United States Patent and Trademark Office on Feb. 19, 1991, now abandoned.

TECHNICAL FIELD

The present invention relates generally to retroviruses, and more specifically, to recombinant retroviruses which are capable of delivering vector constructs to susceptible target cells. These vector constructs are typically designed to express desired proteins in target cells, including proteins which can have a therapeutic effect in a number of ways, and hence, constitute a "drug" transport system for allowing transport of proteins (or RNA) into cells. The specificity of proteins (and RNA) for enzymatic reaction, for binding of cellular components, for immunological action, or for other biological effects, allows for correspondingly specific actions on target cells if the protein or RNA molecule can be transported into the cells. Such actions include the repair of genetic defects, production of antisense RNA to block cellular process, the enzymatic potentiation of prodrugs, and stimulation of the cellular immune system, as well as many other therapies based on the intracellular production of proteins.

BACKGROUND OF THE INVENTION

Retroviruses are RNA viruses which can replicate and integrate into a host cell's genome through a DNA intermediate. This DNA intermediate, or provirus, may be stably integrated into the host's cellular DNA. Due to their efficiency at integrating into host cells, retroviruses are considered to be one of the most promising vectors for use in human gene therapy. These vectors have a number of properties that lead them to be considered as one of the most promising techniques for genetic therapy of disease. These include: (1) efficient entry of genetic material (the vector genome) into cells; (2) an active efficient process of entry into the target cell nucleus; (3) relatively high levels of gene expression; (4) minimal pathological effects on target cells; and (5) the potential to target to particular cellular subtypes through control of the vector-target cell binding and the tissue-specific control of gene expression. For example, a foreign gene of interest may be incorporated into the retrovirus in place of the normal retroviral RNA. When the retrovirus injects its RNA into a cell, the foreign gene is also introduced into the cell, and may then be integrated into the host's cellular DNA as if it were the retrovirus itself. Expression of this foreign gene within the host results in expression of the foreign protein by the host cell.

Most retroviruses which have been developed for gene therapy are murine retroviruses. Briefly, these retroviruses exist in two forms, as proviruses integrated into a host's cellular DNA, or as free virions. The virion form of the virus contains the structural and enzymatic proteins of the retrovirus (including reverse transcriptase), two RNA copies of the viral genome, and portions of the cell's plasma membrane in which is embedded the viral envelope glycoprotein. The genome is organized into four main regions: the Long Terminal Repeat (LTR), and the gag, pol, and env genes. The LTR may be found at both ends of the proviral genome, is a composite of the 5' and 3' ends of the RNA genome, and contains cis-acting elements necessary for the initiation and termination of transcription. The three genes gag, pol, and env are located between the terminal LTRs. The gag and pol genes encode, respectively, internal viral structures and enzymatic proteins. The env gene encodes the envelope glycoprotein which confers infectivity and host range specificity of the virus.

An important consideration in using retroviruses for gene therapy is the availability of "safe" retroviruses. Packaging cell lines have been developed to meet this concern. Briefly, this methodology employs the use of two components, a retroviral vector and a packaging cell. The retroviral vector contains long terminal repeats (LTRs), the foreign DNA to be transferred and a packaging sequence (ψ). This retroviral vector will not reproduce by itself because the genes which encode structural and envelope proteins are not included within the vector. The packaging cell contains genes encoding the gag, pol, and env proteins, but does not contain the packaging signal ψ. Thus, a packaging cell can only form empty virion particles by itself. Within this general method, the retroviral vector is introduced into the packaging cell, thereby creating a "producer cell." This producer cell manufactures virion particles containing only the retroviral vector's (foreign) DNA, and therefore has previously been considered to be a safe retrovirus for therapeutic use.

There are several shortcomings in the current use of this approach. One issue involves the generation of "live virus" (i.e., competent replicating retrovirus) by the producer cell line. Preparations of human therapeutics which are contaminated with retroviruses are not currently considered suitable for use in human therapy. For example, extreme measures are taken to exclude retroviral contamination of monoclonal antibodies for imaging and therapy. Live virus can in conventional producer cells when: (1) The vector genome and the helper genomes recombine with each other; (2) The vector genome or helper genome recombines with homologous cryptic endogenous retroviral elements in the producer cell; or (3) Cryptic endogenous retroviral elements reactivate (e.g., xenotropic retroviruses in mouse cells).

Another issue is the propensity of mouse based producer lines to package endogenous retroviral-vector-like elements (which can contain onc gene sequences) at efficiencies close to that with which they package the desired vector. Such elements, because of their vector-like structure, are transmitted to the target treatment cell at frequencies that parallel its transfer of the desired vector sequence.

A third issue is the ability to make sufficient vector particles at a suitable concentration to:

(1) treat a large number of cells (e.g., $10^8$–$10^{10}$); and (2) manufacture vector particles at a commercially viable cost. Finally, the only producer lines currently used for transfer of genes to human cells are amphotropic producer lines, known for the eponymous murine retroviral envelope gene, which has receptors in most human cells.

In order to construct safer packaging cell lines, researchers have generated additional deletions in the 3' LTR and portions of the 5' LTR (see, Miller and Buttimore, *Mol. Cell. Biol.*, 6:2895–2902, 1986). When such cells are used, two recombination events are necessary to form the wild-type genome. Nevertheless, results from several laboratories have indicated that even when several mutations are present, wild-type virus may still be generated (see, Bosselman et al., *Mol. Cell. Biol.* 7:1797–1806, 1987; Danos and Mulligan, *Proc. Nat'l. Acad. Sci. USA* 81:6460–6464, 1988).

Many of the helper cell lines that have been described to date have been limited to a host cell range of murine, avian, rat and dog cells. While later helper cell lines have been generated using amphotropic retroviral vector systems, which can infect human cells as well as a broad range of other mammalian cells (see, Sorge et al., *Mol. Cell. Biol.* 4:1720–1737, 1984), amphotropic packaging lines developed thus far have retained portions of one or more of the viral LTRs, and, thus, even when multiple mutations are present, have remained capable of generating a replication-competent genome. Amphotropic vector systems with multiple mutations and reduced propensities toward generating infectious virus generally exhibit unsatisfactorily low titres of retroviral particles.

One of the more recent approaches to constructing safer packaging cell lines involves the use of complementary portions of helper virus, divided among two separate plasmids, one containing gag and pol, and the other containing env (see, Markowitz et al., *J. Virol.* 62:1120–1124; and Markowitz et al., *Virology* 167:600–606, 1988. One benefit of this double-plasmid system is that three recombination events are required to generate a replication competent genome. Nonetheless, these double-plasmid vectors have also suffered from the drawback of including portions of the retroviral LTRs, and therefore remain capable of producing infectious virus. Cell lines containing both 3' and 5' LTR deletions have been constructed, but have thus far not proven useful since they produce relatively low titers (Daugherty et al., *J. Virol.* 63:3209–3212, 1989).

The present invention overcomes difficulties of prior packaging cell lines, and further provides other related advantages.

SUMMARY OF THE INVENTION

The present invention provides a method for producing recombinant retroviruses in which the retroviral genome is packaged in a capsid and envelope, preferably through the use of a packaging cell. The packaging cells are provided with viral protein-coding sequences, preferably in the form of two plasmids integrated into the genome of the cell, which produce all proteins necessary for production of viable retroviral particles, a DNA viral construct which codes for an RNA which will carry the desired gene, along with a packaging signal which will direct packaging of the RNA into the retroviral particles.

The present invention additionally provides a number of techniques for producing recombinant retroviruses which can facilitate:

i) the production of higher titres from packaging cells;

ii) the production of higher titres of helper free recombinant retrovirus from packaging cell lines that are non-murine (to avoid production of recombinant or endogenously activated retroviruses, and to avoid packaging of defective murine retroviral sequences) and which will infect human cells;

iii) the production of helper free recombinant retroviruses with higher titres using alternative non-hybrid envelopes such as xenotropic or polytropic envelope proteins (to allow infection of cells poorly infectable with amphotropic recombinant retroviruses or to allow specificity of cell type infection).

iv) packaging of vector constructs by means not involving the use of packaging cells;

v) the production of recombinant retroviruses which can be targeted for preselected cell lines;

vi) the construction of retroviral vectors with tissue-specific (e.g., tumor) promoters; and vii) the integration of the proviral construct into a preselected site or sites in a cell's genome.

One technique for producing higher titres from packaging cells takes advantage of the discovery that of the many factors which can limit titre from a packaging cell, one of the most limiting is the level of expression of the packaging proteins, namely, the gag, pol, and env proteins, as well as the level of expression of the retroviral vector RNA from the proviral vector. This technique allows the selection of packaging cells which have higher levels of expression (i.e., produce higher concentrations) of the foregoing packaging proteins and vector construct RNA. More specifically, this technique allows selection of packaging cells which produce high levels of what is referred to herein as a "primary agent," which is either a packaging protein (e.g., gag, pol, or env proteins) or a gene of interest to be carried into the genome of target cells (typically as a vector construct). This is accomplished by providing in packaging cells a genome carrying a gene (the "primary gene") which expresses the primary agent in the packaging cells, along with a selectable gene, preferably downstream from the primary gene. The selectable gene expresses a selectable protein in the packaging cells, preferably one which conveys resistance to an otherwise cytotoxic drug. The cells are then exposed to a selecting agent, preferably the cytotoxic drug, which enables identification of those cells which express the selectable protein at a critical level (i.e., in the case of a cytotoxic drug, by killing those cells which do not produce a level of resistance protein required for survival).

Preferably, in the technique briefly described above, the expression of both the selectable and primary genes is controlled by the same promoter. In this regard, it may be preferable to utilize a non-MLV retroviral 5' LTR. In order to maximize titre of a recombinant retrovirus from packaging cells, this technique is first used to select packaging cells expressing high levels of all the required packaging proteins, and then is used to select which of these cells, following transfection with the desired proviral construct, produce the highest titres of the recombinant retrovirus.

Techniques are also provided to select cells that produce higher titres of helper free recombinant retroviruses in non-murine cells. These cell lines produce recombinant retroviruses capable of efficiently infecting human cells. These techniques involve screening potential parent cells for their ability to produce recombinant retroviruses in the presence of a replicating virus. Subsequently, uninfected cultures of candidate cell lines chosen by the above procedure are infected with a vector expressing a retroviral gag/pol, and clones which synthesize high levels of gag/pol are identified. A clone of this type is then reinfected with a vector expressing env, and clones expressing high level of env (and gag/pol) are identified. Within the context of the present invention, "high levels" means discernibly greater than that seen in the standard mouse packaging line, PA317 on a Western blot analysis. Many non-mouse cell lines such as human or dog have never been known to spontaneously generate competent retrovirus, do not carry possible recombination partners for recombinant murine retroviral packaging or gene sequences; and do not carry genes which make RNA which may be packaged by the MLV system. Techniques are provided to generate cell lines which produce high titres of recombinant retroviruses using alternative envelopes such as xenotropic or polytropic by techniques similar to those described above. Such retroviruses may be used in infecting amphotropic resistant cells (xenotropic envelope) or infecting only a subset of cells (polytropic).

A technique suitable for producing recombinant retroviruses which can be targeted for preselected cell lines utilizes recombinant retroviruses having one or more of the following: an env gene comprised of a cytoplasmic segment of a first retroviral phenotype, and an extracellular binding segment exogenous to the first retroviral phenotype (the binding segment being from a second viral phenotype or from another protein with desired binding properties which is selected to be expressed as a peptide which will bind to the desired target); another viral envelope protein; another ligand molecule in place of the normal envelope protein; or another ligand molecule along with an envelope protein that does not lead to infection of the target cell type. Preferably, in the technique briefly described above, an env gene comprised of a cytoplasmic segment of a retroviral phenotype is combined with an exogenous gene encoding a protein having a receptor-binding domain to improve the ability of the recombinant retrovirus to bind specifically to a targeted cell type, e.g., a tumor cell. In this regard, it may be preferable to utilize a receptor-binding domain which binds to receptors expressed at high levels on the surface of the target cell (e.g., growth factor receptors in tumor cells) or alternatively, a receptor-binding domain binding to receptors expressed at a relatively higher level in one tissue cell type (e.g., epithelial cells, ductal epithelial cells, etc., in breast cancer). One potential advantage to targeting with hybrid envelopes with specificity for growth factor or activation receptors (like EGF or CD3 receptors is that binding of the vector itself may then lead to cell cycling, which is necessary for viral integration and expression. Within this technique, it may be possible to improve and genetically alter recombinant retroviruses with specificity for a given tumor by repeated passage of a replicating recombinant retrovirus in tumor cells; or by linking the vector construct to a drug resistance gene and selecting for drug resistance.

Techniques for integrating a retroviral genome at a specific site in the DNA of a target cell involve the use of homologous recombination, or alternatively, the use of a modified integrase enzyme which will recognize a specific site on the target cell genome. Such site-specific insertion allows genes to be inserted at sites on the target cells' DNA, which will minimize the chances of insertional mutagenesis, minimize interference from other sequences on the DNA, and allow insertion of sequences at specific target sites so as to reduce or eliminate the expression of an undesirable gene (such as a viral gene) in the DNA of the target cell.

It will be appreciated that any of the above-described techniques may be used independently of the others in particular situations, or can be used in conjunction with one or more of the remainder of the techniques.

These and other aspects of the present invention will become evident upon reference to the following detailed description and attached drawings.

BRIEF DESCRIPTION OF THE DRAWINGS

FIG. 1A depicts four plasmids designed to express retroviral proteins in mammalian cells. pSVgp and pRSVenv are cotransfected with a selectable marker, while pSVgp-DHFR and pRSVenv-phleo are the equivalent plasmids with the selectable marker placed downstream of the viral protein-coding regions.

FIG. 1E depicts the results of Western blot experiments to compare levels of amphotropic env in cell lysates from DA, CA, 2A and PA317.

DETAILED DESCRIPTION OF THE INVENTION

Figure 1B:
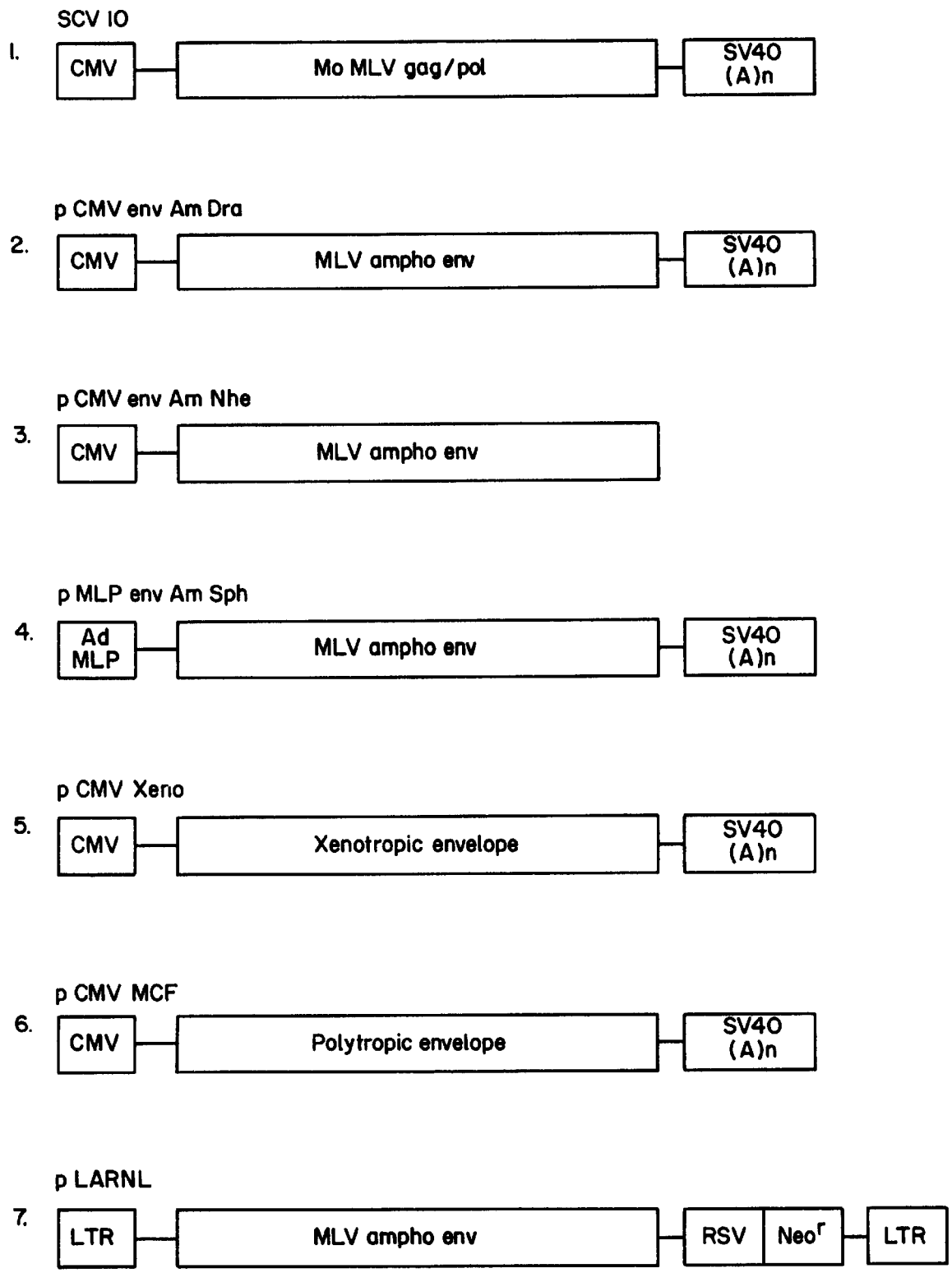
FIG. 1B depicts vectors which lead to expression of: 1. MLV core proteins (pSCV10); 2–4 MLV amphotropic env (pCMVenv AmDra, pCMVenv AnNhe, pMLPenv AmSph); 5. MLV xenotropic env (pCMV xeno). 6. MLV MCFenv (pCMV MCF); 7. MLV amphotropic env as a retroviral vector (pLARNL).
Figure 1C:
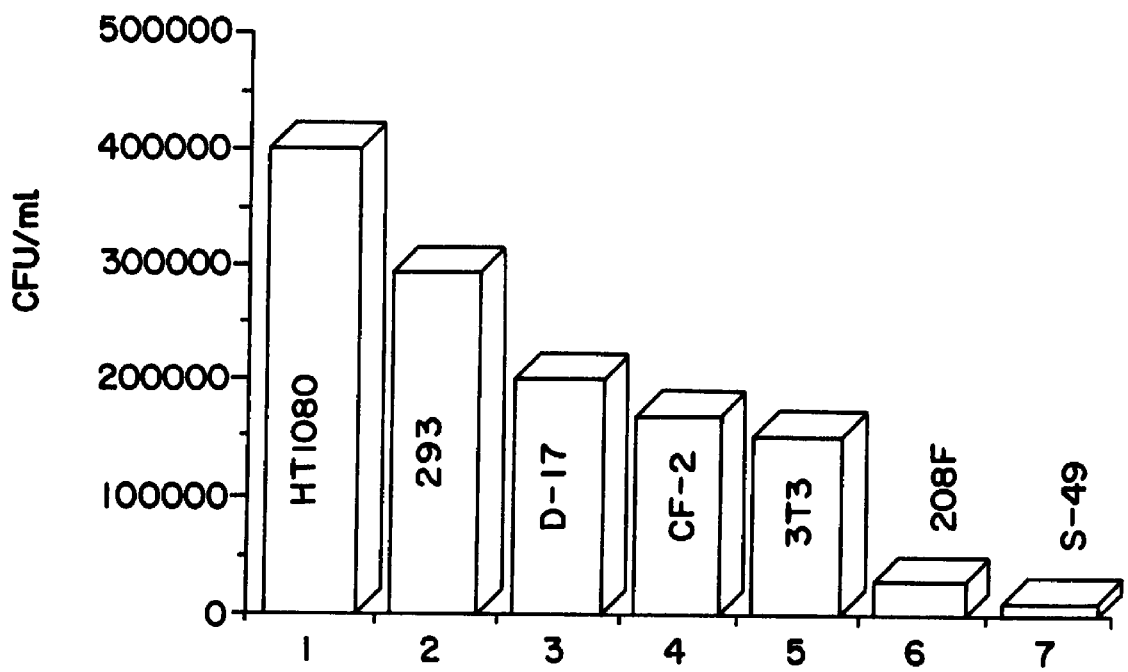
FIG. 1C depicts the results of the screening procedure for assessing the intrinsic ability of cell lines to make retroviral vectors in the presence of helper virus (Example 2B).

In one aspect, the present invention is based, in part, upon the discovery of the major causes of low recombinant virus titres from packaging cell lines (PCL), and of techniques to correct those causes. Basically, at least five factors may be postulated as causes for low recombinant virus titres:

1. the limited availability of viral packaging proteins;
2. the limited availability of retroviral vector RNA genomes;
3. the limited availability of cell membrane for budding of the recombinant retroviruses;
4. the limited intrinsic packaging efficiency of the retroviral vector genome; and 5. the density of the receptor specific for the envelope of a given retrovirus.
6. The limited availability of host cell constituents (such as RNA or myristoylation, phosphorylation, glycosylation or proteolytic functions).

As noted above, the limited availability of viral packaging proteins is the initial limiting factor in recombinant retrovirus production from packaging cells. When the level of packaging protein in the packaging cells is increased, titre increases to about $10^5$ infectious units/milliliter, following which increasing packaging protein level has no further effect on titres. However, titres can be further augmented by also increasing the level of retroviral vector genome available for packaging. Thus, as described herein, it is advantageous to select producer cells that manufacture the maximum levels of packaging proteins and retroviral vector genomes. It has been discovered that the methods of identifying, and thus selecting, packaging cells and producer cells, described earlier under the section entitled "Background of the Invention," tend to lead to selection of many producer cells which produce low titres for the reasons described below.

The present invention takes advantage of the previously disadvantageous fact that the protein expression level of a gene downstream from the 5' LTR or other promoter, and spaced therefrom by an intervening gene, is substantially less than if the intervening gene were absent. In the present invention, the selectable gene is placed downstream from a gene of the packaging genome or the gene of interest carried by the vector construct, but is still transcribed under the control of the viral 5' LTR or other promoter without any splice donor or splice acceptor sites. This accomplishes two things. First, since the packaging genes or genes of interest are now upstream with no intervening gene between themselves and the promoter, their corresponding proteins (packaging protein or protein of interest) will be expressed at a higher level (five- to twentyfold) than the selectable protein. Second, the selectable protein will be expressed on average at a lower level, with the distribution of level of expression shifting toward lower levels. However, the selection level for resistance to phleomycin remains the same, so that only the top-end expressing cells survive. The levels of the packaging protein or of the protein of interest will still be proportional, only in this case, a higher level of selectable protein corresponds to a much higher level of packaging protein or protein of interest.

Preferably, the foregoing procedure is performed using a plasmid carrying one of the proviral gag/pol or env packaging genes, along with a first selectable gene. These cells are then screened for the cells producing the highest levels of protein by reaction with an antibody against gag/pol (or possibly env), a second enzyme or labelled antibody, and then sorted an a fluorescence-activated cell sorter (FACS) or detected on a western blot. Alternatively, other tests for protein level may be used. Subsequently, the procedure and screening are repeated using those selected cells, and the other of the gag/pol or env packaging genes. In this step, a second selectable gene (different from the first) would be required downstream from the packaging gene and the cells producing the largest amount of the second viral protein selected. This cell line is a packaging cell line (PCL) that may be used with any available vector. The procedure and screening are then repeated using the surviving cells, with a plasmid carrying the proviral vector construct bearing the gene of interest and a third selectable gene, different from the first or second selectable gene. As a result of this procedure, cells producing high titres of the desired recombinant retrovirus will be selected, and these can be cultured as required to supply recombinant retrovirus. In addition, gag and pol can be independently introduced and selected.

Example 1 describes the construction of gag/pol and env plasmids designed to use these procedures.

EXAMPLE 1

Plasmids Designed to Make High Levels of Packaging Proteins (FIG. 1)

1. The 2.7 kb Xba I fragment from pPAM (Miller et al., *Mol. Cell. Biol.* 5:431, 1985), which contains the amphotrophic env segment, was cloned in pUC18 at the Xba I site, then removed with Hind III and Sma I. This fragment was cloned into the vector pRSV neo (Gorman et al., *Mol. Cell. Biol.* 2:1044, 1982; Southern et al., *J. Mol. Appl. Genet.* 1:327, 1982) cut with Hind III and Pvu II, to give pRSV env. A 0.7 kb Bam HI to BstE II fragment from the plasmid pUT507 (Mulsant et al., *Somat. Cell. Mol. Genet.* 14:243, 1988) with the BstE II end filled in carries the phleo resistance coding sequence. The 4.2 kb Bam HI to Xho I fragment, the contiguous 1.6 kb Xho I to Xba I (Xba I filled in) from RSVenv, and the phleo fragment were ligated to give pRSVenv-phleo.

2. A fragment from the Pst I site at nucleotide 563 of MLV (*RNA Tumor Viruses*, Vol. II, Cold Spring Harbor, 1985) to the Sca I site at 5870 was derived from pMLV-K (Miller et al., 1985, op. cit.) and cloned in the Pst I to Bam HI (Bam HI filled-in) fragment from p4aA8 (Jolly et al., *Proc. Natl. Acad. Sci. USA* 80:477, 1983) that has the SV40 promoter, the pBR322 ampicillin resistance and origin of replication and the SV40 poly A site. This gives pSVgp. pSVgpDHFR was made using the following fragments: the 3.6 kb Hind III to Sal I fragment from pSVgp containing the SV40 promoter plus MLV gag and some pol sequences; the 2.1 kb Sal I to Sca I fragment from pMLV-K with the rest of the pol gene, the 3.2 kb Xba I (Xba I filled-in) to Pst I fragment from pF400 with the DHFR gene plus poly A site, pBR322 origin and half the ampicillin resistance gene; the 0.7 kb Pst I to Hind III fragment from pBR322 with the other half of the ampicillin resistance gene. This gives pSVgp-DHFR. All these constructs are shown in FIG. 1. These plasmids can be transfected into 3T3 cells or other cells and high levels of gag, pol or env obtained.

An additional method for accomplishing selection is to use a gene selection in one round and its antisense in a subsequent round. For example, gag/pol may be introduced into an HPRT-deficient cell with the HPRT gene and selected for the presence of this gene using that media which requires HPRT for the salvage of purines. In the next round, the antisense to HPRT could be delivered downstream to env and the cell selected in 6 thioguanine for the HPRT-deficient phenotype. Large amounts of antisense HPRT would be required in order to inactivate the HPRT gene transcripts, assuming no reversion occurred. A further method of accomplishing selection is described below. Co-transfection of a 10×stoichiometric excess of the expression vector over the separate selectable marker ensures high copy number of expression vector in drug resistant cell clones. In most of the examples noted herein, the gag/pol and envelope expression vectors were introduced independently (i.e., separate transfections) so that the two structural genes would not recombine or concatamerize (as transfected integrated DNA tends to do), assuring that the genes are unlinked in the genome. The steady-state level of intracellular MLV gag/pol and env was measured by protein immunoblotting. The relative ease, sensitivity, and reproducibility of immunoblotting allowed rapid, quantitative analysis of a large number of cell clones necessary to identify over-expressors of the MLV structural proteins (gag/pol in particular) (see Example 2).

In addition to the gag/pol expressing constructs which begin at nucleotide 563 of MoMLV, several others can be constructed which contain upstream lead sequences. It has been observed by Prats et al. (*RNA Tumor viruses Meeting*, Cold Spring Harbor, N.Y., 1988) that a glycosylated form of the gag protein initiates at nucleotide 357 and a translation enhancer maps in the region between nucleotides 200-270. Therefore, gag/pol expressing constructs may be made beginning at the Bal I site (nucleotide 212) or Eag I site (nucleotide 346) to include these upstream elements and enhance vector production. A preferred method of accomplishing this is to include degenerate mutations to inactivate the packaging signal found here, without affecting the coding potential of the nucleic acid.

Envelope Substitutions

The ability to express gag/pol and env function separately allows for manipulation of these functions independently. A cell line that expresses ample amounts of gag/pol can be used, for example, to address questions of titre with regard to env. One factor resulting in low titres is the density of appropriate receptor molecules on the target cell or tissue. A second factor is the affinity of the receptor for the viral envelope protein. Given that env expression is from a separate unit, a variety of envelope genes (requiring different receptor proteins), such as xenotropic, polytropic, or amphotrophic envs from a variety of sources, can be tested for highest titres on a specific target tissue.

Envelope proteins from one retrovirus can often substitute, to varying degrees, for that of another retrovirus. For instance, the envelope of murine virus 4070A, HTLV I, GALV, and BLV can each substitute for that of MoMLV, albeit with a lower efficiency (Cone and Mulligan, *Proc. Natl. Acad. Sci., USA* 81:6349–53, 1984; Wilson et al., *J. Virol.* 63, 2374–78, 1989; Ban et al., *J. Gen. Virol.* 70:1987–93, 1989). To increase the number of cell types that could be infected with MLV-based vectors, PCLs were generated which individually express either amphotropic, xenotropic, or polytropic envelopes. Vector produced from any of these PCLs can be used to infect any cell which contains the corresponding distinct receptor (Rein and Schultz, *Virology* 136:144–52, 1984). Some cell types may, for instance, lack the amphotropic receptor and thus be resistant to infection with amphotropic vector, but express the xenotropic receptor and therefore be infectable by xenotropic vector. One report suggests that xenotropic vector, in the presence of replication-complement xenotropic virus, may more effectively infect human hematopoietic progenitor cells (Eglitis et al., *Biochem. Biophys. Res. Comm.* 151:201–206, 1988). Xenotropic vector, in the presence of replication-competent xenotropic virus, also infects cells from other species which are not easily infectable by amphotropic virus such as bovine, porcine, and equine (Delouis et al., *Biochem. Biophys Res. Comm.* 169:80–14, 1990). The xenotropic PCLs will therefore be useful for veterinary purposes in these species. Another example would be utilization of the spleen focus-forming virus (SFFV) envelope gene which may allow targeting to cells containing the erythropoietin receptor (J. P. Li et al., *Nature* 343:762–764, 1990).

As a specific example, all of the amphotropic PCLs described herein (canine and human fibroblasts) were infectable by xenotropic vector but were resistant to infection by amphotropic vector, presumably due to the phenomenon of "viral interference" (cf. A. Rein, *Virology* 120:251–57, 1982). The xenotropic PCL therefore allows the facile infection of these amphotropic PCLs, which in turn produces 10–100× higher titre than PCLs whose vector has been introduced by other means (Miller et al., *Somat. Cell Mol. Genet.* 12:175–83, 1986). In principle, a PCL expressing any viral envelope which can function with the MLV vector and packaging system and whose corresponding cellular receptor is found in a given PCL, is useful for allowing vector infection of that PCL.

Vector produced from the polytropic PCL described herein has a more restricted host range on human cells than vector produced from either amphotropic or xenotropic PCLs (see data below). The polytropic PCL may therefore be particularly useful for targeting vector to a specific human cell type. The reduced homology between both xenotropic and polytropic envelopes with the MoMLV gag/pol and with the vector makes these PCLs even less likely to generate replication-competent retrovirus by homologous recombination than amphotropic PCLs. Examples of the use of these methods are set forth below (see Example 2).

Furthermore, envelopes from nonmurine retrovirus sources can be used for pseudotyping a vector. The exact rules for pseudotyping (i.e., which envelope proteins will interact with the nascent vector particle at the cytoplasmic side of the cell membrane to give a viable viral particle (Tato, *Virology* 88:71, 1978) and which will not (Vana, *Nature* 336:36, 1988), are not well characterized. However, since a piece of cell membrane buds off to form the viral envelope, molecules normally in the membrane are carried along on the viral envelope. Thus, a number of different potential ligands can be put on the surface of viral vectors by manipulating the cell line making gag and pol in which the vectors are produced or choosing various types of cell lines with particular surface markers. One type of surface marker that can be expressed in helper cells and that can give a useful vector-cell interaction is the receptor for another potentially pathogenic virus. The pathogenic virus displays on the infected cell surface its virally specific protein (e.g., env) that normally interacts with the cell surface marker or receptor to give viral infection. This reverses the specificity of the infection of the vector with respect to the potentially pathogenic virus by using the same viral protein-receptor interaction, but with the receptors on the vector and the viral protein on the cell.

It may be desirable to include a gene which encodes for an irrelevant envelope protein which does not lead to infection of target cells by the vector so produced, but does facilitate the formation of infectious viral particles. For example, one could use human Sup T1 cells as a helper line. This human T-cell line expresses CD4 molecules at high levels on its surface. Conversion of this into a helper line can be achieved by expressing gag/pol with appropriate expression vectors and also, if necessary, the Moloney ecotropic env gene product as an irrelevant (for human cells) envelope protein (the Moloney ecotropic env only leads to infection of mouse cells). Vectors produced from such a helper line would have CD4 molecules on their surfaces and therefore be capable of infecting only cells which express HIV env, such as HIV-infected cells.

In addition, hybrid envelopes (as described below) can be used in this system as well, to tailor the tropism (and effectively increase titres) of a retroviral vector. A cell line that expresses ample amounts of a given envelope gene can be employed to address questions of titre with regard to gag and pol.

Furthermore, it is also possible to add ligand molecules exogenously to the viral particles which either incorporate themselves in the lipid envelope or can be linked chemically to the lipid or protein constituents.

Cell Lines

The most common packaging cell lines used for MoMLV vector systems (psi2, PA12, PA317) are derived from murine cell lines. There are several reasons why a murine cell line is not the most suitable for production of human therapeutic vectors:

1. They are known to contain endogenous retroviruses, some of which are closely related in sequence and viral type to the MLV vector system used here.
2. They contain nonretroviral or defective retroviral sequences that are known to package efficiently.
3. There may be deleterious effects caused by the presence of murine cell membrane components.

Several non-murine cell lines are potential parents for packaging lines. These include Vero cells which are used in Europe to prepare polio vaccine, WI38 which are used in the U.S. in vaccine production, CHO cells which are used in the U.S. for TPA preparation, D17 or other dog cells that may have no endogenous viruses, and those described in Example 2.

The most important safety concern for the production of retroviral vectors is the inherent propensity of retroviral PCLs to generate replication-competent retrovirus after introduction of a vector (Munchau et al., *Virology* 176:262–65, 1990). This can occur in at least two ways: 1) homologous recombination can occur between the therapeutic proviral DNA and the DNA encoding the MoMLV structural genes ("gag/pol" and "env") present in the PCL (discussed below under "Generation of PCLs"); and 2) generation of replication-competent virus by homologous recombination of the proviral DNA with the very large number of defective endogenous proviruses found in murine cells (Steffen and Weinberg, *Cell* 15:1003–10, 1978); Canaani and Aaronson, *Proc. Natl. Acad. Sci. USA* 76:1677–81, 1979; Stoye and Coffin, *J. Virol.* 61:2659–69 1987). In addition, even murine cell lines lacking vector can produce virus spontaneously or after induction, (e.g., xenotropic virus which can replicate in human cells, Aaronson and Dunn, *J. Virol.* 13:181–85, 1974; Stephenson and Aaronson, *Proc. Natl. Acad. Sci., USA* 71:4925–29, 1974; Aaronson and Stephenson, *Biochem. Biophys. Acta* 458:323–54, 1976). Another safety concern with the utilization of murine cells for the production of murine retroviral vectors is the observation that some of the many endogenous proviral genes (retrovirus-like genes) in the murine genome are expressed, recognized by the retroviral structural gene products of murine PCLs, and delivered and expressed in target cells with an efficiency at least comparable to that of the desired vector (Scolnick et al., *J. Virol.* 29:964–72, 1979; Scadden et al., *J. Virol.* 64:424–27, 1990). These observations strongly suggest that murine cell lines are an unsafe choice for the production of murine retroviral vectors for human therapeutics. To circumvent the inherent safety problems associated with murine cells, PCLs have been generated exclusively from non-murine cell lines (e.g., canine and human cell lines) which are known to lack genomic sequences homologous to that of MoMLV by hybridization analysis (data not shown) (Martin et al., *Proc. Matl. Acad. Sci., USA* 78:4892–96, 1981). Those skilled in the art will recognize that the packaging cells described herein will have a low, but inherent capability of packaging random RNA molecules. Such RNA molecules will not be permanently transmitted to the pseudo-infected target cell.

In addition to issues of safety, the choice of host cell line for the PCL is of importance because many of the physical (such as stability) and biological properties (such as titre) of retroviral particles are dictated by the properties of the host cell. For instance, the host cell must efficiently express (transcribe) the vector RNA genome, prime the vector for first strand synthesis with a cellular tRNA, tolerate and covalently modify the MLV structural proteins (proteolysis, glycosylation, myristylation, and phosphorylation), and the maturing virion buds from the cell membrane, carrying many of the membrane components with it. For example, it has been found that vector made from the mouse packaging line PA317 is retained by a 0.3 micron filter, while that made from the CA line described herein will pass through.

EXAMPLE 2

Packaging Cell Selection

A. MLV structural gene expression vectors

To decrease the possibility of replication-competent virus being generated by genetic interactions between the MLV proviral vector DNA and the structural genes of the PCL, separate expression vectors, each lacking the viral LTR, were generated to express the gag/pol and env genes independently. To further decrease the possibility of homologous recombination with MLV vectors and the resultant generation of replication-competent virus, minimal sequences other than the protein coding sequences were used. In order to express high levels of the MLV structural proteins in the host cells, strong transcriptional promoters (CMV early and Ad5 major late promoters) were utilized. An example of the construction of a MoMLV gag/pol expression vector (pSCV10, see FIG. 1B.1) follows:

1. The 0.7 Kb HinCII/XmaIII fragment encompassing the human cytomegalovirus (CMV) early transcriptional promoter (Boshart et al., *Cell* 41:521–30, 1985) was isolated.
2. A 5.3 Kb PstI(partial)/ScaI fragment from the MoMLV proviral plasmid, MLV-K (Miller et al., *Mol. Cell Biol.* 5:531, 1985) encompassing the entire gag/pol coding region was isolated.
3. A 0.35 Kb DraI fragment from SV40 DNA (residues 2717-2363) encompassing the SV40 late transcriptional termination signal was isolated.
4. Using linkers and other standard recombinant DNA techniques, the CMV promoter-MoMLV gag/pol-SV40 termination signal was ligated into the bluescript vector SK+.

An example of the construction of an MLV amphotropic envelope expression vector (pCMVenvAmDra, see FIG. 1B.2) follows.

1. A 2.7 Kb XbaI/NheI fragment containing the coding sequence of amphotropic envelope from the 4070A proviral clone (Chattopadhyay et al., *J. Virol.* 39:777–91, 1981) was isolated.
2. Using linkers and other standard DNA techniques, the CMV early promoter and SV40 late termination signal described for the gag/pol expression above (pSCV10) were ligated in the order CMV promoter-envelope-termination signal.

A second example of the construction of an MLV amphotropic envelope expression vector (PCMVenvAmNhe, see FIG. 1B.3) follows.

1. A 2.7 Kb XbaI/NheI fragment containing the coding sequence of amphotropic envelope from the 4070A proviral clone described above was isolated.
2. Using linkers and other standard recombinant DNA techniques, the CMV early promoter described for the gag/pol expression above (pSCV10) was ligated in the plasmid pUC18 in the order CMV promoter-envelope (no added transcriptional termination signal).

A third example of the construction of an MLV amphotropic envelope expression vector (pMLPenvAmSph, see FIG. 1B.4) follows.

1. A 0.9 Kb EcoRI/HindIII fragment containing the Adenovirus 5 left end, major late transcriptional promoter, and tripartite leader sequence was isolated.
2. A 0.85 Kb EcoRI/BamHI fragment containing the SV40 small t intron and transcriptional termination signal from clone pJD204 (De Wit et al., *Mol. Cell. Biol.* 7:725–37, 1987) was isolated.
3. A 3 Kb SphI/SmaI fragment containing the coding sequence of amphotropic envelope from the 4070A proviral clone described above was isolated.
4. Using linkers and other standard recombinant DNA techniques, the MLP, amphotropic envelope and the SV40 termination signal were ligated in plasmid pBR322 in the order MLP-envelope-SV40.

An example of the construction of an MLV xenotropic envelope expression vector (pCMMVxeno, see FIG. 1B.5) follows.

1. A 2.2 Kb NaeI/NheI fragment containing the coding region of the xenotropic envelope obtained from clone NZB9-1 (O'Neill et al., *J. Virol.* 53:10–106, 1985) was isolated.
2. Using linkers and other standard recombinant DNA techniques, the CMV early promoter and SV40 late termination signal described for the gag/pol expression above (pSCV10) were ligated in the order CMV promoter-envelope-termination signal.

An example of the construction of an MLV polytropic envelope expression vector (pCMVMCF, see FIG. 1B.6) follows.

1. A 2 Kb BamHI/NheI fragment containing the coding region of the polytropic envelope obtained from clone MCF-247W (Holland et al., *J. Virol.* 53:152–57, 1985) was isolated.
2. Using linkers and other standard recombinant DNA techniques, the CMV early promoter and SV40 late termination signal described for the gag/pol expression above (pSCV10) were ligated in the order CMV promoter-envelope-termination signal.

An example of the construction of an MLV ampho env Neo+ retroviral vector (pLARNL, FIG. 1B.7) follows.

1. The vector pLRNL vector (Emi et al., *J. Virol.* 65:1202–1207, 1991) was digested with BamHI.
2. A 2.7 Kb XbaI fragment containing the envelope protein coding region of retrovirus 4070A (Chattopadhyay et al., *J. Virol.* 39:777–91, 1981) was isolated.
3. Fragments from procedures 1 and 2 above were ligated.

B. Host Cell Selection

Host cell lines were screened for their ability to efficiently (high titre) rescue a drug resistance retroviral vector (A alpha N2) using replication competent retrovirus to produce the gag/pol and env structural genes ("MA" virus). Titre was measured from confluent monolayers 16 h after a medium change by adding filtered supernatants (0.45 um filters) to 5×10$^4$ NIH 3T3 TK$^-$ cells on a 6 cm tissue culture plate in the presence of 4 ug/ml polybrene followed by selection in G418.

Figure 2:
FIG. 2 depicts three sites of fusion of HIV env and MoMLV env after site-directed mutagenesis. The joint at the extracellular margin of the transmembrane region is designated as A, while B and C indicate locations of joints at the middle of the transmembrane region and cytoplasmic margin, respectively. The numbering is according to nucleotide numbers (*RNA Tumor Viruses*, Vol. II, Cold Spring Harbor, 1985). ST, SR, SE are the starts of tat, rev and env while TT, TR, and TE are the corresponding termination sites.
Figure 2:
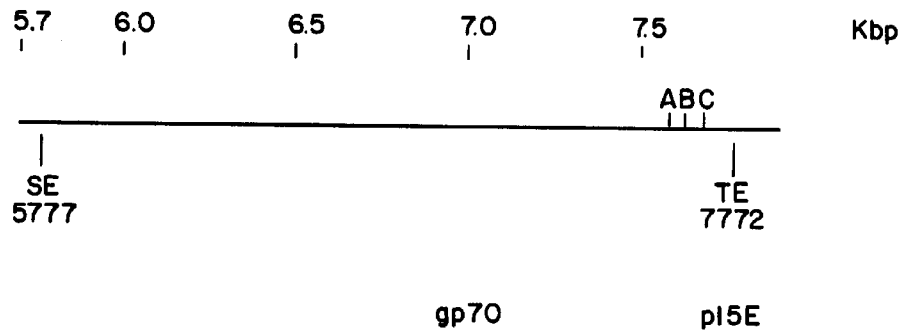

Data from the screening process is shown in FIG. 2. Among the non-murine cell lines which demonstrate the ability to package MoMLV-based vector with high titre are the cell lines CF2, D17, 293, and HT1080. These cell lines were used herein as examples, although any other cells may be tested by such means.

C. Generation of Packaging Cell
   (i) gag/pol intermediate

Figure 1D:
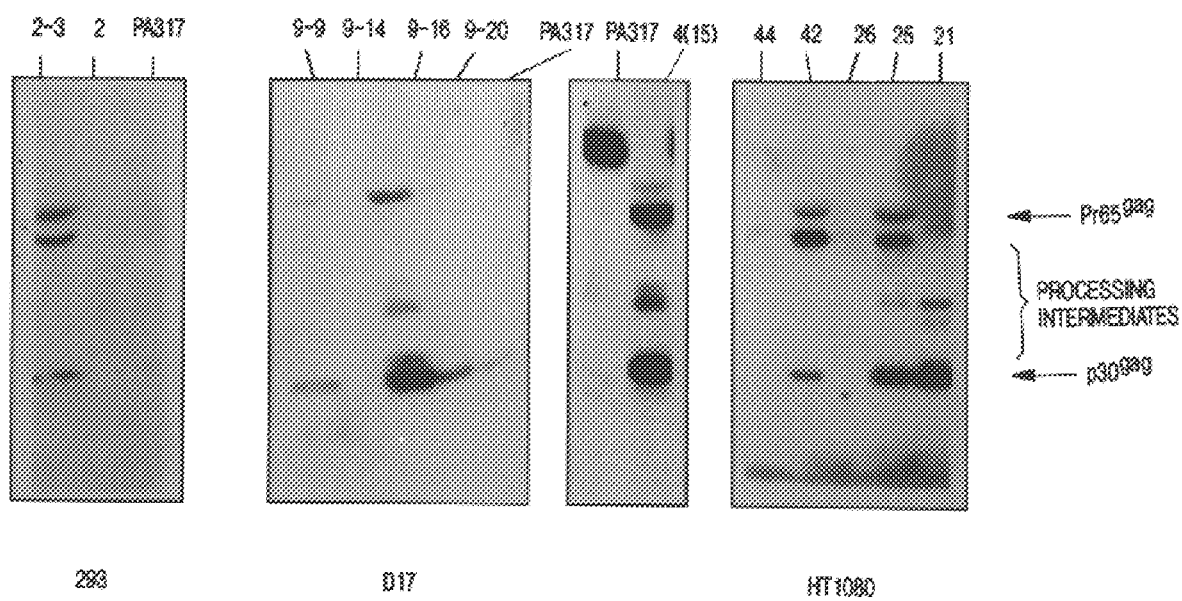
FIG. 1D depicts the results of selecting clones of cells into which pSCV10 had been introduced and examining these clones for gag production as compared to PA317 by Western blots.

As examples of the generation of gag/pol intermediates for PCL production, D17, 293, and HT1080 were co-transfected with 1 ug of the methotrexate resistance vector, pFR400 (Graham and van der Eb, *Virology* 52:456–67, 1973), and 10 ug of the MoMLV gag/pol expression vector, pSCV10 (above) by calcium phosphate co-precipitation (D17 and HT1080, see Graham and van der Eb, *Virology* 52:456–67, 1973), or lipofection (293, see Felgner et al., *Proc. Natl. Acad. Sci., USA* 84:7413–17, 1987). After selection for transfected cells in the presence of the drugs dipyrimidol and methotrexate, individual drug resistant cell colonies were expanded and analyzed for MoMLV gag/pol expression by extracellular reverse transcriptase (RT) activity (modified from Goff et al., *J. Virol.* 38:239–48, 1981) and intracellular p30$^{gag}$ by western blot using anti p30 antibodies (goat antiserum #77S000087 from the National Cancer Institute). This method identified individual cell clones in each cell type which expressed 10 . 50× higher levels of both proteins compared with that of a standard mouse amphotropic PCL, PA317 (FIG. 1D and Table 1).

TABLE 1

PROPERTIES OF MoMLV GAG/POL-EXPRESSING CELLS

| CELL NAME | RT ACTIVITY (CPM) | p30$^{gag}$ EXPRESSION | LARNL TITRE (CFU/ML) |
|---|---|---|---|
| 3T3 | 800 | – | N.D. |
| PA317 | 1350 | +/– | 1.2 × 10$^3$ |
| D17 | 800 | – | N.D. |
| D17 4-15 | 5000 | +++++ | 1.2 × 10$^4$ |
| D17 9-20 | 2000 | +++ | 6.0 × 10$^3$ |
| D17 9-9 | 2200 | ++ | 1.0 × 10$^3$ |
| D17 9-16 | 6100 | +++++ | 1.5 × 10$^4$ |
| D17 8-7 | 4000 | – | N.D. |
| HT1080 | 900 | – | N.D. |
| HTSCV21 | 16400 | +++++ | 8.2 × 10$^3$ |
| HTSCV25 | 7900 | +++ | 2.8 × 10$^3$ |
| HTSCV42 | 11600 | ++ | 8.0 × 10$^2$ |
| HTSCV26 | 4000 | – | <10 |
| 293 | 600 | – | N.D. |
| 293 2-3 | 6500 | +++++ | 7 × 10$^4$ |
| 293 5-2 | 7600 | +++++ | N.D. |

The biological activity of these proteins was tested by introducing a retroviral vector, LARNL (see FIG. 1B) which expresses both the amphotropic envelope and a Neo+ marker which confers resistance to the drug, G418. In every case, co-expression of gag/pol in the cell line and env from the vector allowed efficient packaging of the vector as determined by cell-free transfer of G418 resistance to 3T3 cells (titre). Titre was measured from confluent monolayers 16 h after a medium change by adding filtered supernatants (0.45 um filters) to 5×10$^4$ NIH3T3 TK$^-$ cells on a 6 cm tissue culture plate in the presence of 4 ug/ml polybrene followed by selection in G418. Significantly, the vector titres from the cell lines correlated with the levels of P30$^{gag}$ (Table 1). Since the level of env should be the same in each clone and is comparable to the level found in PA317 (data not shown), this indicates that titre was limited by the lower levels of gag/pol in these cells (including PA317). The titre correlated more closely with the levels of p30$^{gag}$ than with the levels of RT.

(ii) Conversion of gag/pol lines into amphotropic packaging lines

As examples of the generation of amphotropic PCLs, the gag/pol over-expressors for 293 (termed 2–3) and D17 (termed 4–15) were co-transfected by the same techniques described above except that 1 ug of the phleomycin resistance vector, pUT507 (Mulsant et al., *Somat. Cell Mol. Genet.* 14:243–52, 1988), and 10 ug of the amphotropic envelope expression vectors, pMLPenvAmSph (for 2–3) or pCMVenvAmNhe (for 4–15) were used. After selection for transfected cells in the presence of phleomycin, individual drug resistant cell colonies were expanded and analyzed for intracellular gp80$^{env}$ expression by western blot using anti gp70 (goat antiserum #79S000771 from N.C.I.). Several clones were identified which expressed relatively high levels of both gag/pol and ampho env (PCLs, see FIG. 1 for representative data).

In another example of the generation of an ampho PCL, CF2 cells were electroporated (cf. Chu et al., *Nucl. Acids Res.* 15:1311–26, 1987) with 2 ug of the phleomycin resistance marker, pUT507, 10 ug of pSCV10 (above), and 10 ug of pCMVenvAmNhe (above). After selection for transfected cells in the presence of phleomycin, individual drug resistant cell colonies were expanded and analyzed for intracellular expression of MLV p30$^{gag}$ and gp80$^{env}$ proteins by western blot using specific antisera. A clone was identified which expressed relatively high levels of both gag/pol and ampho env (FIG. 1E).

(iii) Performance of amphotropic packaging cell lines.

A number of these ampho PCLs were tested for their capacity to package retroviral vectors by measuring titre after the introduction of retroviral vectors (Table 2). The measurements were performed using uncloned PCLs, so that the average performance of the lines was calculated.

TABLE 2

VECTOR TITRE AND HELPER VIRUS GENERATION IN AMPHOTROPIC PCLs

| CELL TYPE | VECTOR TITRE$^a$ (+/- HELPER VIRUS$^b$) | | |
|---|---|---|---|
| | b-Gal | KT-1 | N2 |
| PA317 | 3.5 × 10$^2$(N.D.) | 1.0 × 10$^4$(N.D.) | 3.0 × 10$^5$(+)$^c$ |
| CA | 5.0 × 10$^4$(N.D.) | 3.0 × 10$^5$(−)$^d$ | 2.0 × 10$^6$(−)$^d$ |
| 2A | 4.0 × 10$^4$(N.D.) | 2.0 × 10$^5$(−)$^e$ | N.D. |
| DA | N.D. | N.D. | 2.0 × 10$^5$(−)$^d$ |
| DA2 | N.D. | 3.9 × 10$^5$(−)$^d$ | N.D. |

$^a$cfu/ml
$^b$as judged by marker rescue assay with MA virus as positive control
$^c$after 20 days in culture
$^d$after 60 days in culture
$^e$after 90 days in culture Highest titres are obtained when retroviral vectors were introduced into PCLs by infection (Miller et al., *Somat. Cell Mol. Genet.* 12:175–83, 1986). However, although ampho-tropic MLV vectors are known to infect these host cell types, the PCLs are blocked for infection by ampho vector since they express ampho env ("viral interference"). To overcome this problem, vectors containing other viral envelopes (such as xenotropic env or VSV G protein, which bind to cell receptors other than the ampho receptor) were generated in the following manner. Ten ug of the vector DNA of interest was co-transfected with 10 ug of DNA which expresses either xeno env (pCMVxeno, above) or a VSV G protein expression vector, MLP G, onto a cell line which expresses high levels of MoMLV gag/pol such as 2–3 cell (see above). The resultant vector containing xenotropic env or VSV G protein, respectively, was produced transiently in the co-transfected cells and after 2 days cell free supernatants were added to the potential PCLs, and vector-infected cells were identified by selection in G418. Both types of vector efficiently infected the ampho-blocked cells and after G418 selection cell free supernatants were collected from the confluent monolayers and titred on NIH 3T3 TK$^-$ cells as described above. The cell clones with the highest titre were chosen as PCLs and referred to as DA (D17 ampho), 2A (293 ampho), and CA (CF2 ampho), respectively. In no case was helper virus detected in the currently described PCLs, even when a retroviral vector (N2) which has a high probability of generating helper virus (Armentano et al., *J. Virol.* 62:1647–50, 1987) was introduced into the PCLs and the cells passaged for as long as 2 months (3 months for vector KT-3). On the other hand, the same vector introduced into the PA317 cell line generated helper virus within 3 weeks of continual passaging.

(iv) Conversion of gag/pol lines into xenotropic packaging cell lines.

Figure 1F:
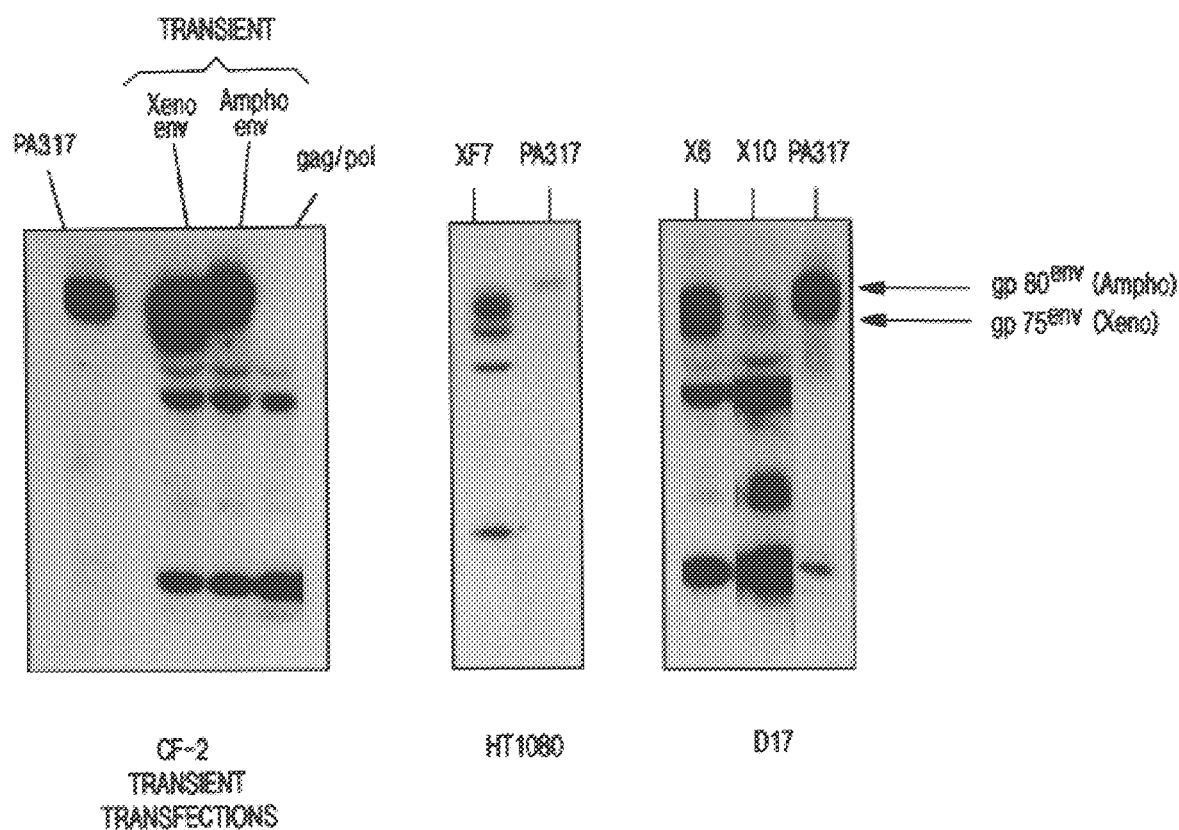
FIG. 1F depicts the results of Western blot experiments to compare levels of xenotropic env in cell lysates from transient transfections of CF gag/pol and permanently expressing lines XF7, X6, X10 and PA317 (ampho env).

As examples of the generation of xenotropic PCLs, the gag/pol over-expressors for D17 (4–15) and HT1080 (SCV21) were co-transfected by the same techniques described above except that 1 ug of either the phleomycin resistance vector, pUT507 (for SCV21), or the hygromycin B resistance marker, pY3 (for 4–15, see Blochlinger and Diggelmann, *Mol. Cell Biol.* 4:2929–31, 1984), and 10 ug of the xenotropic envelope expression vector, pCMVxeno (above) was used. After selection for transfected cells in the presence of phleomycin or hygromycin, respectively, individual drug resistant cell colonies were expanded and analyzed for intracellular expression of MLV p30$^{gag}$ and gp75$^{env}$ proteins by western blot using specific antisera. Clones were identified which expressed relatively high levels of both gag/pol and xeno env (FIG. 1F).

(v) Performance of xenotropic packaging cell lines.

A number of these potential xeno PCLs were tested for their capacity to package retroviral vectors by measuring titre after the introduction of retroviral vectors (Table 3).

TABLE 3

VECTOR TITRE ON XENOTROPIC PCLs

| CELL CLONE | | KT-1 TITRE (CFU/ML) ON HT1080 CELLS |
|---|---|---|
| HT1080 | SCV21 | 1.10 × 10$^5$ |
| | XF1 | 1.0 × 10$^5$ |
| | XF7 | 1.0 × 10$^5$ |
| | XF12 (HX) | 4.5 × 10$^5$ |
| D17 | 4-15 | |
| | X6 | 9.0 × 10$^4$ |
| | X10 (DX) | 1.3 × 10$^5$ |
| | X23 | 8.0 × 10$^4$ |

As described above, vector containing VSV G protein was produced transiently in 2–3 cells. After 2 days, cell free supernatants were added to the xeno PCLs and after G418 selection cell free supernatants were collected from the confluent monolayers and titred as described above except that HT1080 cells, which are infectable by xeno vector, was used instead of NIH 3T3 TK$^-$ cells which are resistant to xeno vector. The cell clones with the highest titre were chosen as PCLs and referred to as DX (D17 xeno) and HX (HT1080 xeno), respectively.

The propensity of the PCLs described above to generate helper virus was tested even more stringently by co-cultivating ampho and xeno PCLs containing the vector, N2. Since ampho vector can infect the xeno PCLs and vice versa, this allows continuous cross-infection events, each of which increases the probability of generating helper virus. As an example, 2A cells containing N2 were co-cultivated with HX cells containing N2. After 23 days, the cultures were still free of ampho and xeno viruses as judged by a vector rescue assay on 293 or Mus dunni cells, both of which can detect ampho and xeno viruses (Table 4).

TABLE 4

HIGH STRINGENCY ANALYSIS FOR PCL TENDENCY TO GENERATE HELPER VIRUS

| TEST MATERIAL | HELPER VIRUS ASSAY |
|---|---|
| AMPHOTROPIC VIRUS | + |
| XENOTROPIC VIRUS | + |
| PA317 + N2 (21d) | + |
| 2A + HX + N2 (23d) | − |

(vi) Conversion of gag/pol lines into polytropic packaging cell lines.

Figure 1G:
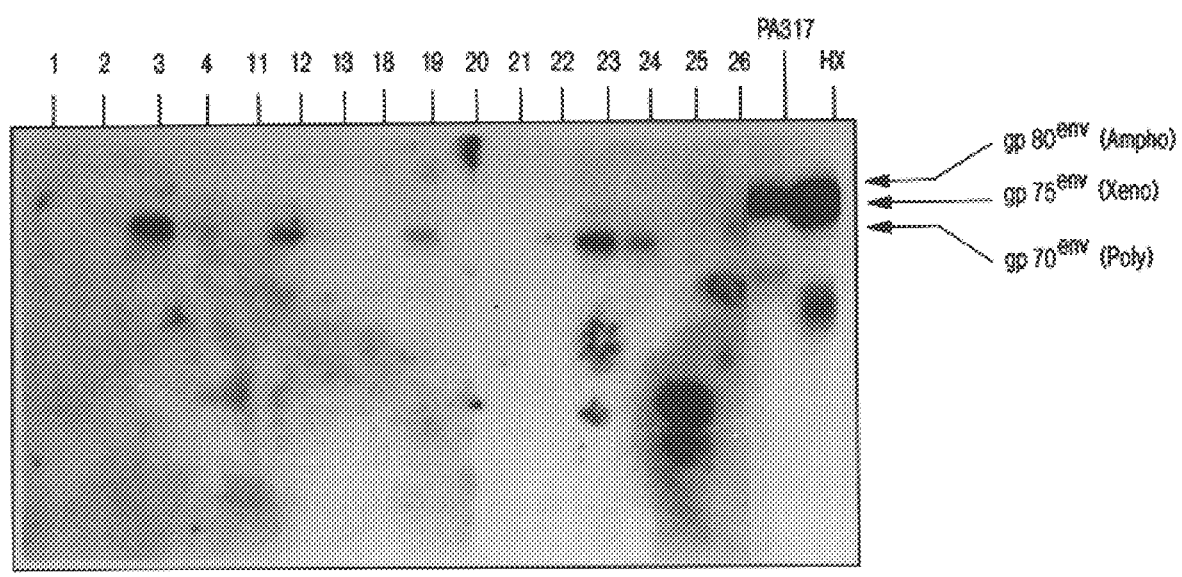
FIG. 1G depicts the results of Western blot experiments to compare levels of MCF (polytropic) env in HT1080 derived clones, PA317 (amphotropic env) and HX (xenotropic env).

As an example of the generation of a polytropic PCL, the gag/pol over-expressor for HT1080 (SCV21) was co-transfected by the same techniques described above, except that 1 ug of the phleomycin resistance vector, pUT507, and 10 ug of the polytropic envelope expression vector, pCMVCF (above) was used. After selection for transfected cells in the presence of phleomycin, individual drug resistant cell colonies were expanded and analyzed for intracellular expression of MLV gp70$^{env}$ protein by western blot using specific antiserum. Clones were identified which expressed relatively high levels of both gag/pol (not shown) and polytropic env (FIG. 1G).

(vii) Performance of polytropic packaging cell lines.

One of these potential poly PCLs (clone 3) was tested for the capacity to package retroviral vectors by measuring titre after the introduction of retroviral vectors (Table 5).

TABLE 5

HOST-RANGE OF POLYTROPIC VECTOR FROM HP CELLS

| CELL LINE | SPECIES | b-Gal TITRE |
|---|---|---|
| 3T3 | MURINE | $1.0 \times 10^4$ |
| PA317 | MURINE | $1.0 \times 10^4$ |
| Mv-1-Lu | MINK | $5.0 \times 10^3$ |
| FRh1 | MACAQUE | <10 |
| HT1080 | HUMAN | <10 |
| HeLa | HUMAN | <10 |
| WI 38 | HUMAN | <10 |
| DETROIT 557 | HUMAN | <10 |
| SUP TI | HUMAN | <10 |
| CEM | HUMAN | <10 |
| U937 | HUMAN | <10 |
| 293 | HUMAN | $2.0 \times 10^4$ |

This cell clone was chosen as PCL and referred to as HP (HT1080 poly). As described above, vector containing VSV G protein was produced transiently in 2–3 cells and after 26 days, cell free supernatants were added to the polytropic PCL (HP). After G418 selection, cell free supernatants were collected from the confluent monolayers and titred as described above on a variety of cell lines. The infection of human cells was very restricted, with all cell lines tested being negative with the exception of 293 cells.

Although the factors that lead to efficient infection of specific cell types by retroviral vectors are not completely understood, it is clear that because of their relatively high mutation rate, retroviruses may be adapted for markedly improved growth in cell types in which initial growth is poor, simply by continual reinfection and growth of the virus in that cell type (the adapter cell). This can also be achieved using viral vectors that encode some viral functions (e.g., env), and which are passed continuously in cells of a particular type which have been engineered to have the functions necessary to complement those of the vector to give out infectious vector particles (e.g., gag/pol). For example, one can adapt the murine amphotropic virus 4070A to human T-cells or monocytes by continuous growth and reinfection of either primary cell cultures or permanent cell lines such as Sup T1 (T-cells) or U937 (monocytes). Once maximal growth has been achieved, as measured by reverse transcriptase levels or other assays of virus production, the virus is cloned out by any of a number of standard methods, the clone is checked for activity (i.e., the ability to give the same maximal growth characteristic on transfection into the adapter cell type) and this genome used to make defective helper genomes and/or vectors which in turn, in an appropriately manufactured helper or producer line, will lead to production of viral vector particles which infect and express in the adapter cell type with high efficiency ($10^7$–$10^9$ infectious units/ml).

VII. Alternative Viral Vector Packaging Techniques

Two additional alternative systems can be used to produce recombinant retroviruses carrying the vector construct. Each of these systems takes advantage of the fact that the insect virus, baculovirus, and the mammalian viruses, vaccinia and adenovirus, have been adapted recently to make large amounts of any given protein for which the gene has been cloned. For example, see Smith et al. (*Mol. Cell. Biol.* 3:12, 1983); Piccini et al. (*Meth. Enzymology,* 13:545, 1987); and Mansour et al. (*Proc. Natl. Acad. Sci. USA* 82:1359, 1985).

These viral vectors can be used to produce proteins in tissue culture cells by insertion of appropriate genes into the viral vector and, hence, could be adapted to make retroviral vector particles.

Adenovirus vectors are derived from nuclear replicating viruses and can be defective. Genes can be inserted into vectors and used to express proteins in mammalian cells either by in vitro construction (Ballay et al., *EMBO J.* 4:3861, 1985) or by recombination in cells (Thummel et al., *J. Mol. Appl. Genetics* 1:435, 1982).

One preferred method is to construct plasmids using the adenovirus Major Late Promoter (MLP) driving: (1) gag/pol, (2) env, (3) a modified viral vector construct. A modified viral vector construct is possible because the U3 region of the 5' LTR, which contains the viral vector promoter, can be replaced by other promoter sequences (see, for example, Hartman, *Nucl. Acids Res.* 16:9345, 1988). This portion will be replaced after one round of reverse transcriptase by the U3 from the 3' LTR.

These plasmids can then be used to make adenovirus genomes in vitro (Ballay et al., op. cit.), and these transfected in 293 cells (a human cell line making adenovirus E1A protein), for which the adenoviral vectors are defective, to yield pure stocks of gag/pol, env and retroviral vector carried separately in defective adenovirus vectors. Since the titres of such vectors are typically $10^7$–$10^{11}$/ml, these stocks can be used to infect tissue culture cells simultaneously at high multiplicity. The cells will then be programmed to produce retroviral proteins and retroviral vector genomes at high levels. Since the adenovirus vectors are defective, no large amounts of direct cell lysis will occur and retroviral vectors can be harvested from the cell supernatants.

Other viral vectors such as those derived from unrelated retroviral vectors (e.g., RSV, MMTV or HIV) can be used in the same manner to generate vectors from primary cells. In one embodiment, these adenoviral vectors are used in conjunction with primary cells, giving rise to retroviral vector preparations from primary cells.

In some cases, gene products from other viruses may be used to improve the properties of retroviral packaging systems. For instance, HIV rev protein might be included to prevent splicing of HIV env or HIV gag/pol MLV vectors or HIV sor might increase the infectivity of T cells by free virus as it does with HIV (See Fischer et al., *Science* 237:868–893, 1987).

In an alternative system (which is more truly extracellular), the following components are used:

1. gag/pol and env proteins made in the baculovirus system in a similar manner as described in Smith et al. (supra) (or in other protein production systems, such as yeast or *E. coli*);
2. viral vector RNA made in the known T7 or SP6 or other in vitro RNA-generating system (see, for example, Flamant and Sorge, *J. Virol.* 62:1827, 1988);
3. tRNA made as in (2) or purified from yeast or mammalian tissue culture cells;
4. liposomes (with embedded env protein); and
5. cell extract or purified necessary components (when identified) (typically from mouse cells) to provide env processing, and any or other necessary cell-derived functions.

Within this procedure (1), (2) and (3) are mixed, and then env protein, cell extract and pre-liposome mix (lipid in a suitable solvent) added. It may, however, be necessary to earlier embed the env protein in the liposomes prior to adding the resulting liposome-embedded env to the mixture of (1), (2), and (3). The mix is treated (e.g., by sonication, temperature manipulation, or rotary dialysis) to allow encapsidation of the nascent viral particles with lipid plus embedded env protein in a manner similar to that for liposome encapsidation of pharmaceuticals, as described in Gould-Fogerite et al., *Anal. Biochem.* 148:15, 1985). This procedure allows the production of high titres of replication incompetent recombinant retroviruses without contamination with pathogenic retroviruses or replication-competent retroviruses.

VIII. Cell Line-Specific Retroviruses—"Hybrid Envelope"

The host cell range specificity of a retrovirus is determined in part by the env gene products. For example, Coffin, J. (*RNA Tumor Viruses* 2:25–27, Cold Spring Harbor, 1985) notes that the extracellular component of the proteins from murine leukemia virus (MLV) and Rous Sarcoma virus (RSV) are responsible for specific receptor binding. The cytoplasmic domain of envelope proteins, on the other hand, are understood to play a role in virion formation. While pseudotyping (i.e., the encapsidation of viral RNA from one species by viral proteins of another species) does occur at a low frequency, the envelope protein has some specificity for virion formation of a given retrovirus. The present invention recognizes that by creating a hybrid env gene product (i.e., specifically, ar. env protein having cytoplasmic regions and exogenous binding regions which are not in the same protein molecule in nature) the host range specificity may be changed independently from the cytoplasmic function. Thus, recombinant retroviruses can be produced which will specifically bind to preselected target cells.

In order to make a hybrid protein in which the receptor binding component and the cytoplasmic component are from different retroviruses, a preferred location for recombination is within the membrane-spanning region of the cytoplasmic component. Example 10 describes the construction of a hybrid env gene which expresses a protein with the CD4 binding portion of the HIV envelope protein coupled to the cytoplasmic domain of the MLV envelope protein.

EXAMPLE 3

Hybrid HIV-MLV Envelopes

A hybrid envelope gene is prepared using in vitro mutagenesis (Kunkel, *Proc. Natl. Acad. Sci. USA* 82:488–492, 1985) to introduce a new restriction site at an appropriate point of junction. Alternatively, if the two envelope sequences are on the same plasmid, they can be joined directly at any desired point using in vitro mutagenesis. The end result in either case is a hybrid gene containing the 5' end of the HIV gp 160 and the 3' end of MLV p15E. The hybrid protein expressed by the resulting recombinant gene is illustrated in FIG. 2 and contains the HIV gp120 (CD4 receptor binding protein), the extracellular portion of HIV gp 41 (the gp 120 binding and fusigenic regions), and the cytoplasmic portion of MLV p15E, with the joint occurring at any of several points within the host membrane. A hybrid with a fusion joint at the cytoplasmic surface (joint C in FIG. 2) causes syncytia when expressed in Sup T1 cells. The number of apparent syncytia are approximately one-fifth that of the nonhybrid HIV envelope gene in the same expression vector. Syncytia with the hybrid occurs only when the rev protein is co-expressed in trans. A hybrid with a fusion joint at the extracellular surface (joint A in FIG. 2) gives no syncytia while hybrid B (in the middle of the transmembrane regions) gives approximately five-fold less syncytium on Sup T1 cells than hybrid C.

While Example 3 illustrates one hybrid protein produced from two different retroviruses, the possibilities are not limited to retroviruses or other viruses. For example, the receptor binding portion of human interleukin-2 may be combined with the envelope protein of MLV to target vectors to cells with IL-2 receptors. In this case, a recombination would preferably be located in the gp 70 portion of the MLV env gene, leaving an intact p15E protein. Furthermore, the foregoing technique may be used to create a recombinant retrovirus with an envelope protein which recognizes antibody Fc segments. Monoclonal antibodies which recognize only preselected target cells only could then be bound to such a recombinant retrovirus exhibiting such envelope proteins so that the retrovirus would bind to and infect only those preselected target cells. Alternatively, a hybrid envelope with the binding domain of avidin would be useful for targeting cells' "images" in a patient or animal with biotinylated antibodies or other ligands. The patient would first be flooded with antibodies, and then antibody binding nonspecifically allowed to clear from the patient's system, before administering the vector. The high affinity ($10^{-15}$) of the avidin binding site for biotin would then allow accurate and efficient targeting to the original tissue identified by the monoclonal "image."

The approach may also be used to achieve tumor-specific targeting and killing by taking advantage of three levels of retroviral vector specificity; namely, cell entry, gene expression, and choice of protein expressed. Retroviral vectors enter cells and exert their effects at intracellular sites. In this respect their action is quite unique. Using this property, and the three levels of natural retroviral specificity (above), retroviral vectors may be engineered to target and kill tumor cells.

The overall goal of targeting of retrovirus to tumor cells may be accomplished by two major experimental routes;

namely, a) selection in tissue culture (or in animals) for retroviruses that grow preferentially in tumor cells; or b) construction of retroviral vectors with tissue (tumor)-specific promoters with improvements being made by in vitro passage, and negative and positive drug-sensitivity selection.

Vectors suitable for selectively infecting selected cell types, such as a tumor cell, may generally be prepared by (a) continuously passaging a virus in cells of the selected cell type until the virus has genetically mutated and a predominant fast growing strain has evolved; (b) isolating the mutated and fast growing strain; (c) identifying and isolating the components of the mutated strain responsible for the preferential growth of the mutated virus; (d) inserting the identified and isolated components as substitutes for counterpart components in a producer cell based upon the virus (prior to continuous passage); and (e) culturing the producer cell to produce the vector.

At least four selective protocols may be utilized to select for retrovirus which grow preferentially in tumor cells; namely, 1) "Env Selection by Passage In Vitro," wherein selection of retrovirus with improved replicative growth ability is accomplished by repeated passage in tumor cells; 2) "Selection with a Drug Resistance Gene," wherein genetic selection for tumor "specific" retroviruses is based on viral constructs containing a linked drug resistance gene; 3) "Hybrid-Env," wherein selection (by protocol #1 or #2, above) of retrovirus with tumor-"specificity" is initiated from a construct containing a hybrid envelope gene which is a fusion of a tumor receptor gene (i.e., an anti-tumor antibody H-chain V-region gene fused with env; or, a growth receptor fused with env); in this case selection begins at a favorable starting point, e.g., an env which has some specificity for tumor cells; or 4) "Selection by Passage In Vitro and Counter Selection by Co-cultivation with Normal Cells," wherein growth in tumor cells is selected-for by repeated passage in mixtures of drug-resistant tumor cells and drug-sensitive normal cells.

With respect to retroviral vector constructs carrying tissue (tumor)-specific promoters, biochemical markers with different levels of tissue-specificity are well known, and genetic control through tissue-specific promoters is understood in some systems. There are a number of genes whose transcriptional promoter elements are relatively active in rapidly growing cells (i.e., transferring receptor, thymidine kinase, etc.) and others whose promoter/enhancer elements are tissue specific (i.e., HBV enhancer for liver, PSA promoter for prostate). Retroviral vectors and tissue-specific promoters (present either as an internal promoter or within the LTR) which can drive the expression of selectable markers and cell cycle genes (i.e., drug sensitivity, Eco gpt; or HSVTK in TK-cells). Expression of these genes can be selected for in media containing mycophenolic acid or HAT, respectively. In this manner, tumor cells containing integrated provirus which actively expresses the drug resistance gene will survive. Selection in this system may involve selection for both tissue-specific promoters and viral LTRs. Alternatively, specific expression in tumor cells, and not in normal cells, can be counter-selected by periodically passaging virus onto normal cells, and selecting against virus that express Eco gpt or HSVtk (drug sensitivity) in those cells (by thioxanthine or acyclovir). Infected cells containing integrated provirus which express Eco gpt or tk phenotype will die and thus virus in that cell type will be selected against.

IX. Site-Specific Integration

Targeting a retroviral vector to a predetermined locus on a chromosome increases the benefits of gene-delivery systems. A measure of safety is gained by direct integration to a "safe" spot on a chromosome, i.e., one that is proven to have no deleterious effects from the insertion of a vector. Another potential benefit is the ability to direct a gene to an "open" region of a chromosome, where its expression would be maximized. Two techniques for integrating retroviruses at specific sites are described below.

(ii) Integrase Modification

Another technique for integrating a vector construct into specific, preselected sites of a target cell's genome involves integrase modification.

The retrovirus pal gene product is generally processed into four parts: (i) a protease which processes the viral gag and pol products; (ii) the reverse transcriptase; and (iii) RNase H, which degrades RNA of an RNA/DNA duplex; and (iv) the endonuclease or "integrase."

The general integrase structure has been analyzed by Johnson et al. (*Proc. Natl. Acad. Sci. USA* 83:7648–7652, 1986). It has been proposed that this protein has a zinc binding finger with which it interacts with the host DNA before integrating the retroviral sequences.

In other proteins, such "fingers" allow the protein to bind to DNA at particular sequences. One illustrative example is the steroid receptors. In this case, one can make the estrogen receptor, responding to estrogens, have the effect of a glucocorticoid receptor, responding to glucocorticoids, simply by substituting the glucocorticoid receptor "finger" (i.e., DNA binding segment) in place of the estrogen receptor finger segment in the estrogen receptor gene. In this example, the position in the genome to which the proteins are targeted has been changed. Such directing sequences can also be substituted into the integrase gene in place of the present zinc finger. For instance, the segment coding for the DNA binding region of the human estrogen receptor gene may be substituted in place of the DNA binding region of the integrase in a packaging genome. Initially, specific integration would be tested by means of an in vitro integration system (Brown et al., *Cell* 29:347–356, 1987). To confirm that the specificity would be seen in vivo, this packaging genome is used to make infectious vector particles, and infection of and integration into estrogen-sensitive and estrogen-nonsensitive cells compared in culture.

Through use of this technique, incoming viral vectors may be directed to integrate into preselected sites on the target cell's genome, dictated by the genome-binding properties of site-specific DNA-binding protein segments spliced into the integrase genome. It will be understood by those skilled in the art that the integration site must, in fact, be receptive to the fingers of the modified integrase. For example, most cells are sensitive to glucocorticoids and hence their chromatin has sites for glucocorticoid receptors. Thus, for most cells, a modified integrase having a glucocorticoid receptor finger would be suitable to integrate the proviral vector construct at those glucocorticoid receptor-binding sites.

X. Production of Recombinant Retroviral Vectors in Transgenic Animals

Figure 3:
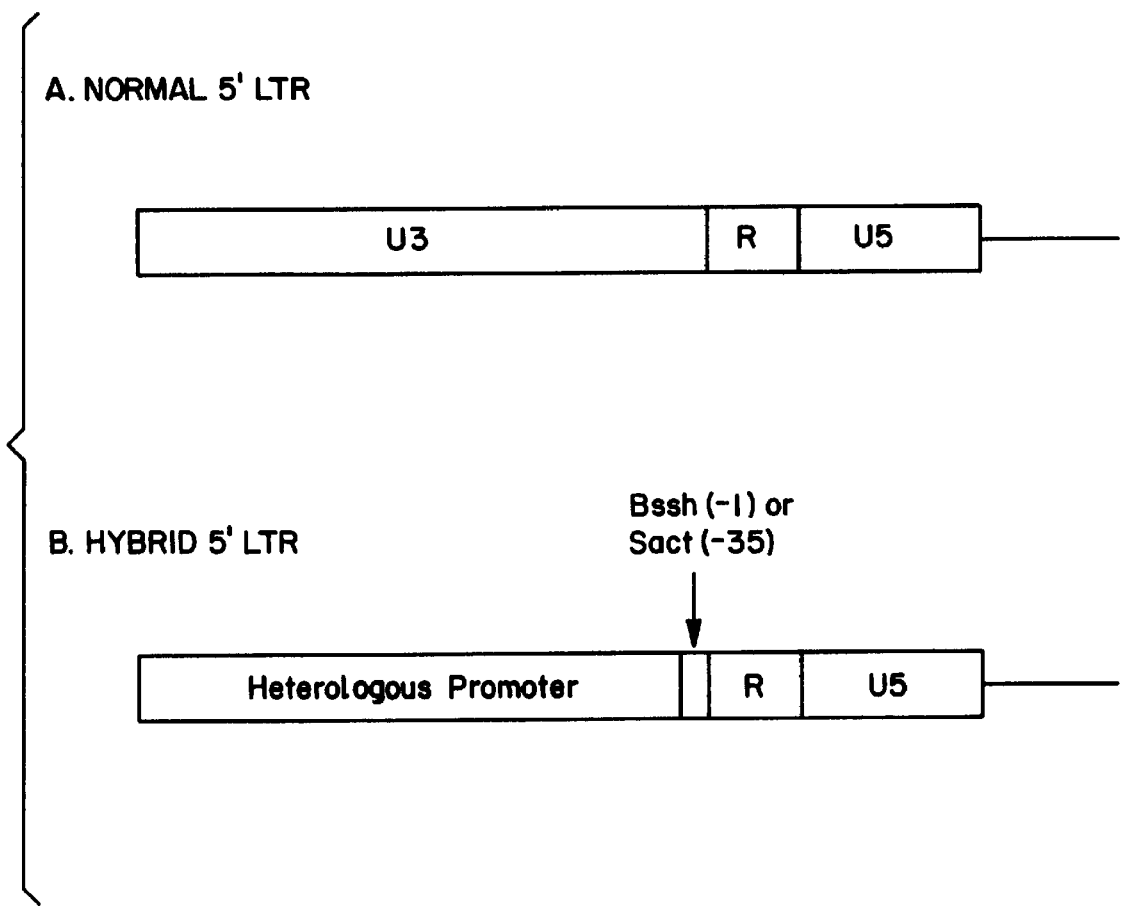
FIG. 3 depicts the substitution of U3 in a 5' LTR by a heterologous promoter/enhancer in which can be fused to either the Sac I, Bssh II or other site in the region.
Figure 4:
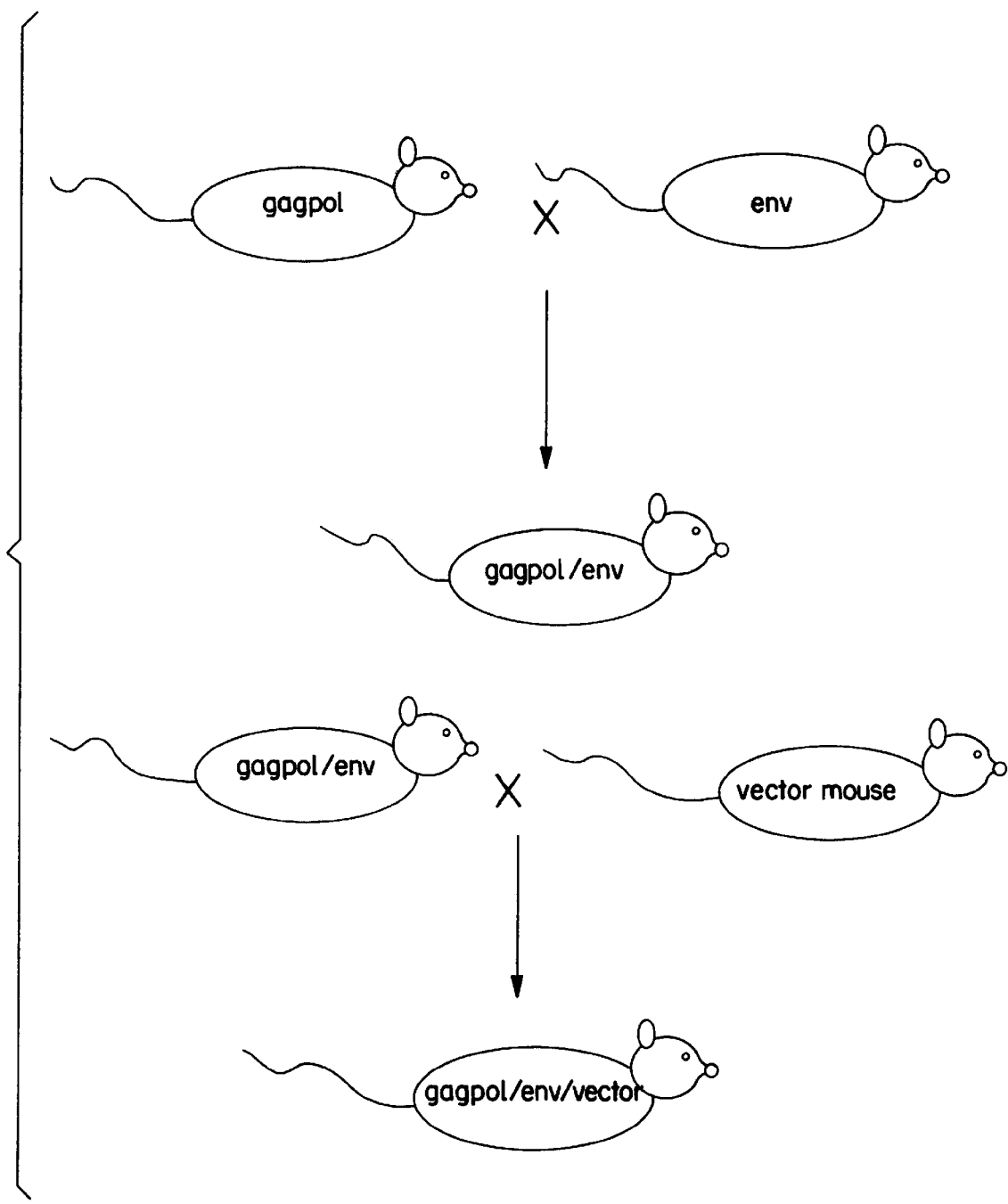
FIG. 4 illustrates a representative method for crossing transgenic mice expressing viral protein or vector RNA.

Two problems previously described with helper line generation of retroviral vectors are: (a) difficulty in generating large quantities of vectors; and (b) the current need to use permanent instead of primary cells to make vectors. These problems can be overcome with producer or packaging lines that are generated in transgenic animals. These animals would carry the packaging genomes and retroviral vector genomes. Current technology does not allow the generation of packaging cell lines and desired vector-producing lines in primary cells due to their limited life span. The current technology is such that extensive characterization is necessary, which eliminates the use of primary cells because of senescence. However, individual lines of transgenic animals can be generated by the methods provided herein which produce the packaging functions, such as gag, pol or env. These lines of animals are then characterized for expression in either the whole animal or targeted tissue through the selective use of housekeeping or tissue-specific promoters to transcribe the packaging functions. The vector to be delivered is also inserted into a line of transgenic animals with a tissue-specific or housekeeping promoter. As discussed above, the vector can be driven off such a promoter substituting for the U3 region of the 5' LTR (FIG. 3). This transgene could be inducible or ubiquitous in its expression. This vector, however, is not packaged. These lines of animals are then mated to the gag/pol/env animal and subsequent progeny produce packaged vector. The progeny, which are essentially identical, are characterized and offer an unlimited source of primary producing cells. Alternatively, primary cells making gag/pol and env and derived from transgenic animals can be infected or transfected in bulk with retrovirus vectors to make a primary cell producer line. Many different transgenic animals or insects could produce these vectors, such as mice, rats, chickens, swine, rabbits, cows, sheep, fish and flies. The vector and packaging genomes would be tailored for species infection specificity and tissue-specific expression through the use of tissue-specific promoters and different envelope proteins. An example of such a procedure is illustrated in FIG. 4.

Although the following examples of transgenic production of primary packaging lines are described only for mice, these procedures can be extended to other species by those skilled in the art. These transgenic animals may be produced by microinjection or gene transfer techniques. Given the homology to MLV sequences in mice genome, the final preferred animals would not be mice.

EXAMPLE 4

Production of Gag/Pol Proteins Using Housekeeping Promoters for Ubiquitous Expression in Transgenic Animals An example of a well-characterized housekeeping promoter is the HPRT promoter. HPRT is a purine salvage enzyme which expresses in all tissues. (See Patel et al., *Mol. Cell Biol.* 6:393–403, 1986 and Melton et al., *Proc. Natl. Acad. Sci.* 81:2147–2151, 1984). This promoter is inserted in front of various gag/pol fragments (e.g., Bal I/Sca I; Aat II/Sca I; Pst I/Sca I of MoMLV; see *RNA Tumor Viruses* 2, Cold Spring Harbor Laboratory, 1985) that are cloned in Bluescript plasmids (Strategene, Inc.) using recombinant DNA techniques (see Maniatis et al., *Molecular Cloning: A Laboratory Manual*, Cold Spring Harbor, 1982). The resulting plasmids are purified (Maniatis et al., op. cit.) and the relevant genetic information isolated using Geneclean (Bio 101) or electroelution (see Hogan et al. (eds.), *Manipulating the Mouse Embryo: A Laboratory Manual*, Cold Spring Harbor, 1986).

These fully characterized DNAs are microinjected in the pronucleus of fertilized mouse ova at a concentration of 2 ug/ml. Live-born mice are screened by tail blot analyses (see Hogan et al., op. cit.). Transgenic-positive animals are characterized for expression levels of gag/pol proteins by immunoprecipitation of radiolabeled primary cells, such as fibroblast (see Harlow et al. (eds.), *Antibodies: A Laboratory Manual*, Cold Spring Harbor, 1988). Animals then bred to homozygosity for establishment of animal lines that produce characterized levels of gag/pol.

EXAMPLE 5

Production of env Proteins/Hybrid Envelope Proteins Using Housekeeping Promoters for Ubiquitous Expression in Transgenic Animals This example utilizes the HPRT promoter for expression of either envelope or hybrid envelope proteins. The envelope proteins can be from any retrovirus that is capable of complementing the relevant gag/pol, in this case that of MLV. Examples are ecotropic MLV, amphotrophic MLV, xenotropic MLV, polytropic MLV, or hybrid envelopes. As above, the envelope gene is cloned behind the HPRT promoter using recombinant DNA techniques (see Maniatis et al., op. cit.). The resulting "minigene" is isolated (see Hogan et al., op. cit.), and expression of envelope protein is determined (Harlow et al., op. cit.). The transgenic envelope animals are bred to homozygosity to establish a well-characterized envelope animal.

EXAMPLE 6

Production of gag/pol-env Animals Using Housekeeping Promoters for Ubiquitous Expression in Transgenic Animals This uses the well-characterized gag/pol animals, as well as the animals for the establishment of a permanent gag/pol/envelope animal line. This involves breeding to homozygosity and the establishment of a well-characterized line. These lines are then used to establish primary mouse embryo lines that can be used for packaging vectors in tissue culture. Furthermore, animals containing the retroviral vector are bred into this line.

EXAMPLE 7

Production of Tissue-Specific Expression of gag/pol-env or Hybrid Envelope in Transgenic Animals This example illustrates high level expression of the gag/pol, envelope, or hybrid envelope in specific tissues, such as T-cells. This involves the use of CD2 sequences (see Lang et al., *EMBO J.* 7:1675–1682, 1988) that give position and copy number independence. The 1.5 kb Bam HI/Hind III fragment from the CD2 gene is inserted in front of gag/pol, envelope, or hybrid envelope fragments using recombinant DNA techniques. These genes are inserted into fertilized mouse ova by microinjection. Transgenic animals are characterized as before. Expression in T-cells is established, and animals are bred to homozygosity to establish well-characterized lines of transgenic animals. Gag/pol animals are mated to envelope animals to establish gag/pol-env animals expressing only in T-cells. The T-cells of these animals are then a source for T-cells capable of packaging retroviral vectors. Again, vector animals can be bred into these gag/pol-env animals to establish T-cells expressing the vector.

This technique allows the use of other tissue-specific promoters, such as milk-specific (whey), pancreatic (insulin or elastase), or neuronal (myelin basic protein) promoters. Through the use of promoters, such as milk-specific promoters, recombinant retroviruses may be isolated directly from the biological fluid of the progeny.

EXAMPLE 8

Production of Either Housekeeping or Tissue-Specific Retroviral Vectors in Transgenic Animals The insertion of retroviruses or retroviral vectors into the germ line of transgenic animals results in little or no expression. This effect, described by Jaenisch (see Jahner et al., *Nature* 28:623–628, 1982), is attributed to methylation of 5' retroviral LTR sequences. This technique would overcome the methylation effect by substituting either a housekeeping or tissue-specific promoter to express the retroviral vector/retrovirus. The U3 region of the 5' LTR, which contains the enhancer elements, is replaced with regulatory sequences from housekeeping or tissue-specific promoters (see FIG. 20). The 3' LTR is fully retained, as it contains sequences necessary for polyadenylation of the viral RNA and integration. As the result of unique properties of retroviral replication, the U3 region of the 5' LTR of the integrated provirus is generated by the U3 region of the 3' LTR of the infecting virus. Hence, the 3' is necessary, while the 5' U3 is dispensable. Substitution of the 5' LTR U3 sequences with promoters and insertion into the germ line of transgenic animals results in lines of animals capable of producing retroviral vector transcripts. These animals would then be mated to gag/pol-env animals to generate retroviral-producing animals (see FIG. 4).

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An enveloped vector particle comprising:
    gag and pol proteins from a retrovirus;
    a nucleic acid sequence associated with said vector particle;
    an envelope having vesicular stomatitis virus (VSV) G envelope glycoprotein therein.

2. The vector particle of claim 1, wherein said gag and pol proteins are from the same species of retrovirus.

3. The vector particle of claim 2, wherein the nucleic acid sequence encodes a gene having an origin other than from said retrovirus, said gene being expressible into polypeptide.

4. The vector particle of claim 3, in which said polypeptide is a selectable marker.

5. The vector particle of claim 4, wherein the selectable marker is expressed by a neomycin resistance gene.

6. The vector particle of claim 3, wherein said nucleic acid sequence additionally comprises a promoter which can direct the transcription of said gene.

7. The vector particle of claim 2, wherein said gag and pol proteins are from MoMLV.

8. A method of introducing foreign nucleic acid into a cell, said method comprising
    infecting said cell with the enveloped vector particle of claim 1.

9. The method of claim 8, wherein said gag and pol proteins are from the same species of retrovirus.

10. The method of claim 9, wherein said cell is outside the normal host range of the retrovirus.

11. A method according to claim 9, wherein the retrovirus has a host range not including human cells or a subset of human cells.

12. A method according to claim 9, wherein the retrovirus is MoMLV.

13. A cell line that stably expresses or carries gag/pol, transfected or transduced with a nucleic acid molecule encoding a retroviral vector and a nucleic acid molecule encoding a VSV G protein, the cell line being capable of producing functional vector particles.

14. The cell line of claim 13, wherein the cell line is transiently transfected.

15. A 293 cell stably expressing gag/pol.

16. The cell of claim 15, wherein the cell is a 293 2–3 cell.

17. A method of making a VSV G pseudotyped virus, comprising:
    introducing into a cell line that stably expresses gag/pol a VSV G protein expression vector and a retroviral vector construct, the resulting cell line being capable of producing vector particles comprising VSV G protein.

18. The method of claim 17, wherein the retroviral vector construct is introduced prior to the VSV G protein expression vector.

19. The method of claim 18, wherein the method further comprises selecting for cells carrying the retroviral vector construct prior to introducing the VSV G protein expression vector.

20. A method of making a VSV G pseudotyped virus, comprising:
    (a) cotransfecting or sequentially transfecting a cell with a vector that directs the expression of gag/pol and a retroviral vector construct; and
    (b) introducing a VSV G protein expression vector into the cotransfected or sequentially transfected cell, the resulting cell being capable of producing vector particles comprising VSV G protein.

21. The method of claim 20, wherein the cell is cotransfected, and the method includes selecting for transfected cells prior to introducing a VSV G protein expression vector.

22. The method of claim 20, wherein the cell is sequentially transfected, and the method include selecting for cells expressing either gag/pol or the retroviral vector construct.

* * * * *

UNITED STATES PATENT AND TRADEMARK OFFICE
CERTIFICATE OF CORRECTION

PATENT NO. : 5,817,491

DATED : October 6, 1998

INVENTOR(S) : Jiing-Kuan Yee; Nobuhiko Emi; Theordore Friedmann; Douglas Jolly; Jack Barber It is certified that error appears in the above-identified patent and that said Letters Patent is hereby corrected as shown below:

On the title page,

Please correct the title on U.S. Patent No. 5,817,491 to read -- VSV G PSEUDOTYPED RETROVIRAL VECTORS--

Please correct the inventor information to read --Jiing-Kuan Yee, Del Mar, Calif.; Nobuhiko Emi, Nagoya, Japan; Theordore Friedmann, La Jolla, Calif.; Douglas J. Jolly, Leucadia, Calif.; Jack R. Barber, San Diego, Calif.--.

Signed and Sealed this

Eleventh Day of May, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,817,491

DATED : October 6, 1998

INVENTOR(S) : Yee, et al.

It is certified that error appears in the above-identified patent and that said Letters Patent is hereby corrected as shown below:

```
                         column 1, line 30, just before the heading
"TECHNICAL FIELD", insert the following section:

--GOVERNMENT SUPPORT

This invention was made with Government support under Grant Nos.
AI28945, CA58317 and HD20034, awarded by the National Institutes of
Health.  The Government may have certain rights in this invention.--
```

Signed and Sealed this

Eighth Day of June, 1999

Attest:

Q. TODD DICKINSON

*Attesting Officer*              *Acting Commissioner of Patents and Trademarks*